United States Patent
Gao et al.

(10) Patent No.: US 11,786,464 B2
(45) Date of Patent: Oct. 17, 2023

(54) PH RESPONSIVE BLOCK COPOLYMER COMPOSITIONS AND MICELLES THAT INHIBIT MCT 1 AND RELATED PROTEINS

(71) Applicant: The Board of Regents of the University of Texas System, Austin, TX (US)

(72) Inventors: Jinming Gao, Dallas, TX (US); Tongyi Huang, Dallas, TX (US); Qiang Feng, Allen, TX (US); Baran Sumer, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 17/239,742

(22) Filed: Apr. 26, 2021

(65) Prior Publication Data

US 2021/0338579 A1    Nov. 4, 2021

Related U.S. Application Data

(60) Provisional application No. 63/015,260, filed on Apr. 24, 2020.

(51) Int. Cl.

| | | |
|---|---|---|
| *A61K 9/107* | (2006.01) | |
| *A61K 47/32* | (2006.01) | |
| *A61K 47/34* | (2017.01) | |
| *A61K 31/5025* | (2006.01) | |
| *A61K 45/06* | (2006.01) | |
| *A61P 35/00* | (2006.01) | |
| *A61K 31/519* | (2006.01) | |
| *B82Y 5/00* | (2011.01) | |

(52) U.S. Cl.
CPC ........ *A61K 9/1075* (2013.01); *A61K 31/5025* (2013.01); *A61K 31/519* (2013.01); *A61K 45/06* (2013.01); *A61K 47/32* (2013.01); *A61K 47/34* (2013.01); *A61P 35/00* (2018.01); *B82Y 5/00* (2013.01)

(58) Field of Classification Search
CPC ...... A61K 47/32; A61K 49/0082; A61P 35/00
See application file for complete search history.

(56) References Cited

U.S. PATENT DOCUMENTS

| | | |
|---|---|---|
| 6,660,793 B1 | 12/2003 | McIntyre et al. |
| 9,751,970 B2 | 9/2017 | Gao et al. |
| 10,017,598 B2 | 7/2018 | Gao et al. |
| 2006/0034796 A1 | 2/2006 | Ashwell et al. |
| 2006/0229235 A1 | 10/2006 | Peterson |
| 2008/0081075 A1 | 4/2008 | Hsiue et al. |
| 2009/0028788 A1 | 1/2009 | Achilefu |
| 2009/0317802 A1 | 12/2009 | Bhatia et al. |
| 2010/0069726 A1 | 3/2010 | Levinson |
| 2010/0303731 A1 | 12/2010 | Hyde et al. |
| 2010/0311903 A1 | 12/2010 | Rajagopalan |
| 2011/0305660 A1 | 12/2011 | Stayton et al. |
| 2012/0070399 A1 | 3/2012 | Jegou |
| 2013/0330278 A1 | 12/2013 | Gao et al. |
| 2013/0331426 A1 | 12/2013 | Gao et al. |

FOREIGN PATENT DOCUMENTS

| | | |
|---|---|---|
| CS | 225516 | 6/1983 |
| GB | 475131 | 11/1937 |
| GB | 1174148 | 12/1969 |
| WO | WO 2002/100439 | 12/2002 |
| WO | WO 2003/074026 | 9/2003 |
| WO | WO 2009/095569 | 8/2009 |
| WO | WO 2009/138473 | 11/2009 |
| WO | WO 2009/140429 | 11/2009 |
| WO | WO 2010/116063 | 10/2010 |
| WO | WO 2011/097384 | 8/2011 |
| WO | WO 2012/039741 | 3/2012 |
| WO | WO 2012/039855 | 3/2012 |
| WO | WO 2012/040513 | 3/2012 |

OTHER PUBLICATIONS

Yu, "Intracellular pH-activated PEG-b-PDPA wormlike micelles for hydrophobic drug delivery", Polym. Chem., 2013, 4, 5052.*
Alani et al., "Polymeric micelles for the pH-dependent controlled, continuous low dose release of paclitaxel," *Biomaterials*, 31:1765-772, 2010.
Albertazzi et al., "Delivery and subcellular targeting of dendrimer-based fluorescent pH sensors in living cells," *J Am Chem Soc.*, 132:18158-67, 2010.
Almutairi et al., "Biodegradable pH-sensing dendritic nanoprobes for near-infrared fluorescence lifetime and intensity imaging," *J Am Chem Soc.*, 130:444-5, 2008.
Bae et al., "Design of environment-sensitive supramolecular assemblies for intracellular drug delivery: polymeric micelles that are responsive to intracellular pH change," *Angew Chem Int Ed Engl.*, 42:4640-4643, 2003.
Bae et al., "Multifunctional polymeric micelles with folate-mediated cancer cell targeting and pH-triggered drug releasing properties for active intracellular drug delivery," *Mol BioSyst.*, 1:242-250, 2005.
Bae et al., "Preparation and Biological Characterization of Polymeric Micelle Drug Carriers with Intracellular pH-Triggered Drug Release Property: Tumor Permeability, Controlled Subcellular Drug Distribution, and Enhanced in Vivo Antitumor Efficacy," *Bioconjug Chem.*, 16:122-30, 2005.
Benjaminsen et al., "Evaluating nanoparticle sensor design for intracellular pH measurements," *ACS Nano*, 5:5864-73, 2011.
Blanco et al., "β-Lapachone-containing PEG-PLA Polymer Micelles as Novel Nano therapeutics against NQO1-Overexpressing Tumor Cells," *J Control Release*, 122(3):365-374, 2007.
Braunecker et al., "Controlled/living radical polymerization: Features, developments, and perspectives," *Progress in Polymer Science*, 32(1):93-146, 2007.

(Continued)

*Primary Examiner* — Sahar Javanmard
(74) *Attorney, Agent, or Firm* — Parker Highlander PLLC

(57) ABSTRACT

Described herein are therapeutic pH responsive compositions comprising a block copolymer and a therapeutic agent useful for the treatment of cancer.

13 Claims, 12 Drawing Sheets

(56) References Cited

OTHER PUBLICATIONS

Bütün et al., "Synthesis and aqueous solution properties of near-monodisperse tertiary amine methacrylate homopolymers and diblock copolymers," *Polymer*, 42:5993-6008, 2001.
Casey et al., "Sensors and regulators of intracellular pH," *Nat Rev Mol Cell Biol.*, 11:50-61, 2010.
Chenna et al., "Preparation and cytotoxicity toward cancer cells of mono(arylimino) derivatives of beta-lapachone," *J Med Chem.*, 44:2486-2489, 2001.
De Silva et al., "Signaling recognition events with fluorescent sensors and switches," *Chem Rev.*, 97:1515-1566, 1997.
Diaz-Fernandez et al., "Micelles for the self-assembly of "off-on-off" fluorescent sensors for pH windows," *Chemistry—A European Journal*, 12(3):921-930, 2006.
Extended European Search Report issued in European Application No. 17205562.6, dated May 9, 2018.
Extended European Search Report issued in European Application No. 16204435.8, dated Apr. 10, 2017.
Extended European Search Report issued in European Patent Application No. 11 82 7074, dated Feb. 26, 2014.
Ghosh et al., "Simultaneous and reversible functionalization of copolymers for biological applications," *Macromolecules*, 39:5595-5597, 2006.
Giacomelli et al., "Specific interactions improve the loading capacity of block copolymer micelles in aqueous media," *Langmuir*, 23:6947-6955, 2007.
Griset et al., "Expansile nanoparticles: synthesis, characterization, and in vivo efficacy of an acid-responsive polymeric drug delivery system," *J Am Chem Soc.*, 131:2469-2471, 2009.
Habraken et al., "Thiol chemistry on well-defined synthetic polypeptides," *Chem Comm.*, 24:3612-3614, 2009.
Han et al., "Fluorescent indicators for intracellular pH," *Chem Rev.*, 110(5):2709-28, 2010.
Heffernan et al., "Polyketal nanoparticles: a new pH-sensitive biodegradable drug delivery vehicle," *Bioconjugate Chem.*, 16:1340-1342, 2005.
Hu et al., "Synthesis and pH-dependent micellization of 2-(diisopropylamino)ethyl methacrylate based amphiphilic diblock copolymers via RAFT polymerization," *Polymer*, 48:3437-3443, 2007.
Huang et al., "Tumor-Targeted Inhibition of Monocarboxylate Transporter 1 Improves T-Cell Immunotherapy of Solid Tumors", Adv. Healthcare Mater. 20, p. 2000549 (2021).
Izumi et al., "Cellular pH regulators: potentially promising molecular targets for cancer chemotherapy," *Cancer Treat Rev.*, 29(6):541-9, 2003.
Jung et al., "pH-sensitive polymer nanospheres for use as a potential drug delivery vehicle," *Biomacromolecules*, 8:3401-7, 2007.
Kato et al., "Polymerization of methyl methacrylate with the carbon tetrachloride/dichlorotris-(triphenylphosphine)ruthedum(II)/methylaluminum bis(2,6-di-tert-butylphenoxide) initiating system: possibility of living radical polymerization," *Macromolecules*, 28:1721-1723, 1995.
Khan et al. "Targeting metabolic activity in high-risk neuroblastoma through Monocarboxylate Transorter 1 (MCT1) inhibition", Oncogene 39(17):pp. 3555-3570 (Apr. 1, 2020).
Khemtong et al., "In vivo off-resonance saturation magnetic resonance imaging of $\alpha_\nu\beta_3$-targeted superparamagnetic nanoparticles," *Cancer Res.*, 69:1651-1658, 2009.
Kim et al., "Doxorubicin loaded pH-sensitive micelle: antitumoral efficacy against ovarian A2780/DOXR tumor," *Pharm Res.*, 25:2074-82, 2008.
Kim et al., "Multicenter phase II trial of Genexol-PM, a novel Cremophor-free, polymeric micelle formulation of paclitaxel, with cisplatin in patients with advanced non-small-cell lung cancer," *Ann Oncol.*, 18(12):2009-14, 2007.
Kobayashi et al., "New strategies for fluorescent probe design in medical diagnostic imaging," *Chem Rev.*, 110(5):2620-40, 2010.
Kobayashi et al., "Target-cancer-cell-specific activatable fluorescence imaging probes: rational design and in vivo applications," *Acc Chem Res.*, 44(2):83-90, 2011.
Lakowicz, "Chapter 13. Energy Transfer," *Principles of Fluorescence Spectroscopy*, $3^{rd}$ ed., New York City: Springer, 2006. 443-475. Print.
Lee et al., "Activatable imaging probes with amplified fluorescent signals," *Chem Commun.*, 36:4250-60, 2008.
Lee et al., "Doxorubicin loaded pH-sensitive polymeric micelles for reversal of resistant MCF-7 tumor," *J Control Release*, 103:405-18, 2005.
Lee et al., "Poly(L-histidine)-PEG block copolymer micelles and pH-induced destabilization," *J Control Release*, 90:363-74, 2003.
Li et al., "pH-activated near-infrared fluorescence nanoprobe imaging tumors by sensing the acidic microenvironment," *Adv Funct Mater.*, 20:2222-2230, 2010.
Licciardi et al., "Synthesis of novel folic acid-functionalized biocompatible block copolymers by atom transfer radical polymerization for gene delivery and encapsulation of hydrophobic drugs," *Biomacromolecules*, 6:1085-1096, 2005.
Liu et al. "Nanocomplexes loaded with miR-128-3p for enhancing chemotherapy effect of colorectal cancer through dual-targeting silence the activity of P13K/AKT and MEK/ERK pathway," Drug Delivery, 27(1): pp. 323-333 (Feb. 2020).
Lopalco et al., "Catch and release microwave mediated synthesis of cyanine dyes," *Org Biomol Chem.*, 7:856-859, 2009.
Lovell et al., "Activatable photosensitizers for imaging and therapy," *Chem Rev.*, 110(5):2839-57, 2010.
Ma et al., "Well-defined biocompatible block copolymers via atom transfer radical polymerization of 2-methacryloyloxyethyl phosphorylcholine in protic media," *Macromolecules*, 36(10):3475-3484, 2003.
Marconescu, "Targeting nanoparticles to tumor vasculature," *PhD Thesis*, UT Southwestern Medical Center, Dallas, 2008.
Maxfield et al., "Endocytic recycling," *Nat Rev Mol Cell Biol.*, 5(2)121-32, 2004.
McAllister et al., "Polymeric nanogels produced via inverse microemulsion polymerization as potential gene and antisense delivery agents," *J Am Chem Soc.*, 124:15198-15207, 2002.
Moad et al., "Living radical polymerization by the RAFT process," *Australian Journal of Chemistry*, 58(6):379-410, 2005.
Modi et al., "A DNA nanomachine that maps spatial and temporal pH changes inside living cells," *Nat Nanotech.*, 4:325-330, 2009.
Nakanishi et al., "Development of the polymer micelle carrier system for doxorubicin," *J Control Release*, 74:295-302, 2001.
Nasongkla et al., "Multifunctional polymeric micelles as cancer-targeted, MRI-ultrasensitive drug delivery systems," *Nano Lett.*, 6:2427-2430, 2006.
Nishi et al., "The vacuolar (H+)-ATPases—nature's most versatile proton pumps," *Nat Rev Mol Cell Biol.*, 3(2):94-103, 2002.
Office Action issued in Australian Application No. 2011306076, dated May 1, 2014.
Office Action issued in Australian Application No. 2011306079, dated Feb. 27, 2015.
Office Action issued in Australian Application No. 2015203892, dated Aug. 3, 2015.
Office Action issued in Australian Application No. 2016203456, dated Feb. 7, 2017.
Office Action issued in Australian Application No. 2017272262, dated Nov. 30, 2018.
Office Action issued in Canadian Application No. 2,811,692, dated Nov. 20, 2017.
Office Action issued in European Application No. 11827074.3, dated Jan. 8, 2015.
Office Action issued in European Application No. 11827074.3, dated Nov. 26, 2015.
Office Action issued in European Application No. 16204435.8, dated Jan. 30, 2018.
Office Action issued in Japanese Application No. 2013-530130, dated Jul. 8, 2015. (English translation of Japanese text).
Office Action issued in Japanese Application No. 2013-530130, dated May 16, 2016, and English language translation thereof.
Office Action issued in Japanese Application No. 2016-175152, dated Jul. 11, 2018, and English language translation thereof.

(56) References Cited

OTHER PUBLICATIONS

Office Action issued in Japanese Application No. 2016-175152, dated Sep. 6, 2017, and English language translation thereof.
Office Action issued in U.S. Appl. No. 13/825,518, dated Apr. 30, 2015.
Office Action issued in U.S. Appl. No. 13/825,518, dated Jan. 21, 2015.
Office Action issued in U.S. Appl. No. 13/825,518, dated Sep. 18, 2015.
Office Action issued in U.S. Appl. No. 15/072,522, dated May 26, 2016.
Office Action issued in U.S. Appl. No. 15/072,522, dated Oct. 13, 2016.
Office Action issued in U.S. Appl. No. 16/006,885, dated Dec. 28, 2018.
Office Action issued in U.S. Appl. No. 16/006,885, dated Mar. 18, 2019.
Office Action issued in U.S. Appl. No. 16/006,885, dated Sep. 11, 2019.
Office Action issued in U.S. Appl. No. 16/006,885, dated Sep. 8, 2020.
Office Action issued in U.S. Appl. No. 16/814,803, dated Aug. 5, 2020.
Office Action issued in U.S. Appl. No. 16/814,803, dated May 29, 2020.
Office Action issued in U.S. Appl. No. 16/814,803, dated Nov. 12, 2020.
Office Action issued in U.S. Appl. No. 16/814,898, dated Jan. 14, 2021.
PCT International Preliminary Report on Patentability issued in International application No. PCT/US2011/001418, dated Apr. 4, 2013.
PCT International Preliminary Report on Patentability issued in International application No. PCT/US2011/047497, dated Apr. 4, 2013.
PCT International Preliminary Report on Patentability issued in International Application No. PCT/US2013/035050, dated Oct. 16, 2014.
PCT International Search Report and Written Opinion issued in International Application No. PCT/US2021/029046, dated Aug. 24, 2021.
PCT International Search Report and Written Opinion issued in International application No. PCT/US2011/001418, dated Dec. 2, 2011.
PCT International Search Report and Written Opinion issued in International application No. PCT/US2011/047497, dated Oct. 21, 2011.
PCT International Search Report and Written Opinion issued in International Application No. PCT/US2013/035050, dated Sep. 10, 2013.
Qiao et al., "The use of PEGylated poly [2-(N,N-dimethylamino) ethyl methacrylate] as a mucosal DNA delivery vector and the activation of innate immunity and improvement of HIV-1-specific immune responses", Biomaterials, 31(1):pp. 115-123 (2010).
Reinicke et al., "Develoment of beta-Lapachone prodrugs for therapy against human cancer cells with elevated NAD(P)H:Quinone Oxidoreductase 1 levels," *Clin Cancer Res.*, 11:3055-3064, 2005.

Seshadri et al., "The delivery of superoxide dismutase encapsulated in polyketal microparticles to rat myocardium and protection from myocardial ischemia-reperfusion injury," *Biomaterials*, 31:1372-1379, 2010.
Srikun et al., "A dendrimer-based platform for simultaneous dual fluorescence imaging of hydrogen peroxide and pH gradients produced in living cells," *Chemical Science*, 2:1156-1165, 2011.
Sun et al., "Bright fluorescent nanoparticles for developing potential optical imaging contrast agents," *Nanoscale*, 2:548-558, 2010.
Sutton et al., "Doxorubicin and beta-lapachone release and interaction with micellar core materials: experiment and modeling," *Exp Biol Med.*, 232(8):1090-9, 2007.
Sutton et al., "Functionalized micellar systems for cancer targeted drug delivery," *Pharmaceutical Research*, 24(6):1029-1049, 2007.
Sutton, "Chapter 5: Hydrophobic prodrug strategy for the creation of polymeric micelles with pHsensitive release of beta-lapachone," *pH Sensitive RNA and Drug Delivery Systems—Ph.D. Dissertation*, Case Western Reserve University, Cleveland, 2007. 174-206.
Sy et al., "Surface functionalization of polyketal microparticles with nitrilotriacetic acid-nickel complexes for efficient protein capture and delivery," *Biomaterials*, 31:4987-4994, 2010.
Tsarevsky et al., "'Green' atom transfer radical polymerization: from process design to preparation of well-defined environmentally friendly polymeric materials," *Chem. Rev.*, 107(6):2270-99, 2007.
Uchiyama et al., "Multiplexing sensory molecules map protons near micellar membranes," *Angew Chem Int Ed Engl.*, 47(25):4667-9, 2008.
Ueno et al., "Fluorescent probes for sensing and imaging," *Nat methods*, 8(8):642-5, 2011.
Urano et al., "Selective molecular imaging of viable cancer cells with pH-activatable fluorescence probes," *Nat Med.*, 15:104-109, 2009.
Vamvakaki et al., "Synthesis of controlled structure water-soluble diblock copolymers via oxyanionic polymerization," *Macromolecules*, 32:2088-2090, 1999.
Vetvicka et al., "Biological evaluation of polymeric micelles with covalently bound doxorubicin," *Bioconjug Chem.*, 20:2090-2097, 2009.
Wang et al., "Controlled living radical polymerization—atom-transfer radical polymerization in the presence of transition-metal complexes," *J Am. Chem Soc.*, 117:5614-5615, 1995.
Webb et al., "Dysregulated pH: a perfect storm for cancer progression," *Nat Rev Cancer*, 11(9):671-7, 2011.
Ye et al., "Novel near-infrared fluorescent integrin-targeted DFO analogue," *Bioconjug Chem.*, 19:225-234, 2007.
Yezhelyev et al., "Proton-sponge coated quantum dots for siRNA delivery and intracellular imaging," *J Am Chem Soc.*, 130(28):9006-12, 2008.
Yu et al., "Overcoming endosomal barrier by amphotericin B-loaded dual pH-responsive PDMA-b-PDPA micelleplexes for siRNA delivery," *ACS Nano*, 5(11):9246-55, 2011.
Zhang et al., "Creating new fluorescent probes for cell biology," *Nat Rev Mol Cell Biol.*, 3(12):906-18, 2002.
Zhou et al., "Tunable, ultra-sensitive pH responsive nanoparticles targeting specific endocytic organelles in living cells," *Angew Chem Int Ed Engl.*, 50:6109-6114, 2011.

\* cited by examiner

PH RESPONSIVE BLOCK COPOLYMER COMPOSITIONS AND MICELLES THAT INHIBIT MCT 1 AND RELATED PROTEINS

This application claims the benefit of priority to U.S. Provisional Application No. 63/015,260, filed on Apr. 24, 2020, the entire contents of which are hereby incorporated by reference.

This invention was made with government support under Grant No. U54 CA244719 awarded by the National Institutes of Health. The government has certain rights in the invention.

BACKGROUND OF THE INVENTION

Multifunctional nanoparticles have received attention in a wide range of applications such as biosensors, diagnostic nanoprobes and targeted drug delivery systems. These efforts have been driven to a large extent by the need to improve biological specificity with reduced side effects in diagnosis and therapy through the precise, spatiotemporal control of agent delivery in various physiological systems. In order to achieve this goal, efforts have been dedicated to develop stimuli-responsive nanoplatforms. Environmental stimuli that have been exploited for pinpointing the delivery efficiency include pH, temperature, enzymatic expression, redox reaction and light induction. Among these activating signals, pH trigger is one of the most extensively studied stimuli based on two types of pH differences: (a) pathological (e.g. tumor) vs. normal tissues and (b) acidic intracellular compartments.

For example, due to the unusual acidity of the tumor extracellular microenvironment (pH~6.5), several pH-responsive nano systems have been reported to increase the sensitivity of tumor imaging or the efficacy of therapy. However, for polymer micelle compositions that release drug by hydrolysis in acidic environments, it can take days for the release of the drug. In that time period, the body can excrete or break down the micelles.

To target the acidic endo-/lysosomal compartments, nanovectors with pH-cleavable linkers have been investigated to improve payload bioavailability. Furthermore, several smart nanovectors with pH-induced charge conversion have been designed to increase drug efficacy. The endocytic system is comprised of a series of compartments that have distinctive roles in the sorting, processing and degradation of internalized cargo. Selective targeting of different endocytic compartments by pH-sensitive nanoparticles is particularly challenging due to the short nanoparticle residence times (<mins) and small pH differences in these compartments (e.g. <1 pH unit between early endosomes and lysosomes. Ultra pH sensitive (UPS) nanoparticles remain as intact micelles at physiological pH (7.4) during blood circulation but disassembles when the environmental pH is reduced below the micelle transition pH ($pH_t$) upon exposure to tumor acidic milieu.

AZD3965 is a small molecule drug developed by AstraZeneca that specifically inhibits monocarboxylate transporter 1 (MCT 1) (FIG. 2a). Previous report on the mechanism of action was mainly attributed to the accumulation of intracellular lactic acid, which leads to a decrease of intracellular pH and feedback inhibition of glycolysis, thereby deterring the proliferation of tumor cells. The effect of MCT 1 inhibition on the tumor microenvironment and resulting influence on anti-tumor immunity is not clear. A challenge in the clinical use of AZD3965 arises from dose-limiting toxicities in the heart and/or eye tissues, where MCT 1 expression is high, due to non-specific drug distribution from oral administration. Adverse side effects such as rise of cardiac troponin levels and electroretinogram changes have been observed. Tumor-targeted delivery of AZD3965 exploiting tumor acidotic metabolism has the potential to increase the therapeutic window of the drug while allowing the investigation of MCT 1 inhibition on antitumor immunity.

What is needed are improved pH-responsive compositions for therapeutic applications, in particular compositions having increased drug payloads, prolonged blood circulation times, rapid delivery of drug at the target site, and responsiveness within specific narrow pH ranges (e.g. for targeting of tumors or specific organelles). pH sensitive micelles can maximize the efficacy of a drug payload, for example a monocarboxylate transporter (MCT) inhibitor, by targeted delivery to tumor areas of greatest corresponding activity and thus most susceptible to inhibition.

SUMMARY OF THE INVENTION

Block copolymers described herein are therapeutic agents useful for the treatment of primary and metastatic tumor tissue (including lymph nodes). The block copolymers and micelle compositions presented herein exploit this ubiquitous pH difference between cancerous tissue and normal tissue and provides a highly sensitive and specific response after being taken up by the cells, thus, allowing the deployment of a therapeutic payload to tumor tissues.

In certain embodiments provided herein is a micelle, comprising:
(i) a block copolymer, or a pharmaceutically acceptable salt, solvate, or hydrate thereof, the block copolymer comprising:
a hydrophilic polymer segment (Ia):

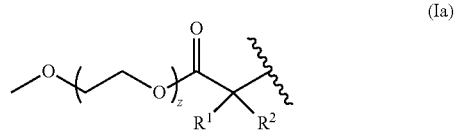

(Ia)

wherein $n_1$ is an integer from 10-200; and
a hydrophobic polymer segment (Ib) covalently bound to the hydrophilic polymer segment (I):

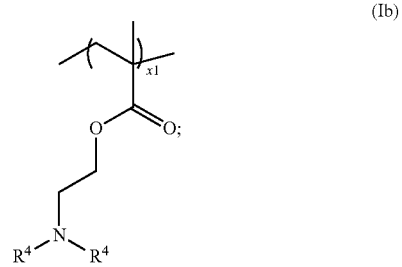

(Ib)

wherein x1 is an integer from 20-300;
wherein:
$R^1$ and $R^2$ are each independently hydrogen or an optionally substituted $C_1$-$C_6$ alkyl;
$R^3$ and $R^4$ are each independently an optionally substituted $C_1$-$C_6$ alkyl, $C_3$-$C_{10}$ cycloalkyl or aryl;
or $R^3$ and $R^4$ are taken together with the corresponding nitrogen to which they are attached form an optionally substituted 5 to 7-membered ring; and (ii) a therapeutic agent encapsulated by the block copolymer, wherein the therapeutic agent is a monocarboxylate transport inhibitor.

In certain embodiments, provided herein is a micelle, comprising:
(i) a block copolymer of Formula (I), or a pharmaceutically acceptable salt, solvate, or hydrate:

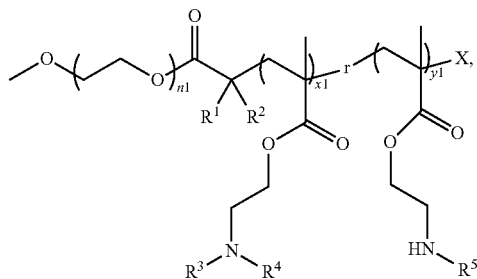

(I)

wherein:
$n_1$ is an integer from 10-200;
$x_1$ is an integer from 20-300;
$y_1$ is an integer from 0-10;
X is a halogen, —OH, or —C(O)OH;
$R^1$ and $R^2$ are each independently hydrogen or optionally substituted $C_1$-$C_6$ alkyl;
$R^3$ and $R^4$ are each independently an optionally substituted $C_1$-$C_6$ alkyl, $C_3$-$C_{10}$ cycloalkyl or aryl;
or $R^3$ and $R^4$ are taken together with the corresponding nitrogen to which they are attached form an optionally substituted 5 to 7-membered ring;
$R^5$ is hydrogen or a fluorescent dye; and
(ii) a therapeutic agent encapsulated by the block copolymer, wherein the therapeutic agent is a monocarboxylate transport inhibitor.

In certain embodiments, provided herein is a micelle, comprising:
(i) a block copolymer of Formula (II), or a pharmaceutically acceptable salt, solvate, hydrate, or isotopic variant thereof:

Formula (II)

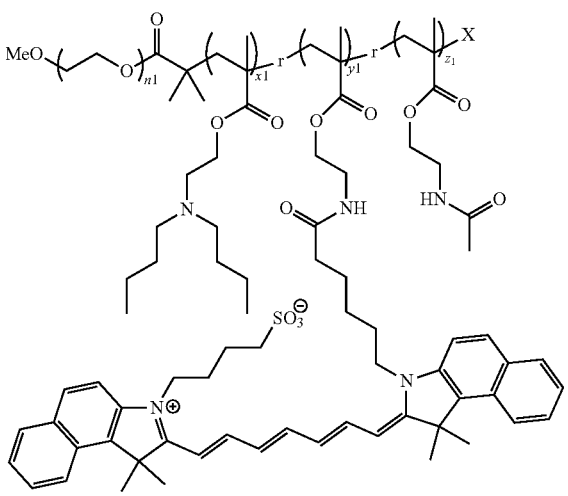

wherein:
$X^1$ is a halogen, —OH, or —(O)OH;
n is 90-140;
$x_1$ is 50-200;
$y_1$ is 0-3; and
$z_1$ is 0-3.
and
(ii) a therapeutic agent encapsulated by the block copolymer, wherein the therapeutic agent is a monocarboxylate transport inhibitor.

In some embodiments, the of the block copolymer of Formula (I), $R^1$ and $R^2$ are each independently an optionally substituted $C_1$-$C_6$ alkyl. In some embodiments, $R^1$ and $R^2$ are each independently —CH3. In some embodiments, $R^3$ and $R^4$ are each independently an optionally substituted $C_1$-$C_6$ alkyl. In some embodiments, $R^3$ and $R^4$ are each independently —CH$_2$CH$_3$, —CH$_2$CH$_2$CH$_3$, or —CH$_2$CH$_2$CH$_2$CH$_3$. In some embodiments, $R^3$ and $R^4$ are taken together with the corresponding nitrogen to which they are attached form an optionally substituted 5 to 7-membered ring. In some embodiments, $R^3$ and $R^4$ taken together are —CH$_2$(CH$_2$)$_2$CH$_2$—, —CH$_2$(CH$_2$)$_3$CH$_2$—, or —CH$_2$(CH$_2$)$_4$CH$_2$—. In some embodiments, $R^5$ is hydrogen. In some embodiments, $y_1$ is an integer from 1-9, 1-8, 1-7, 1-6, 1-5, 1-4, or 1-3. In some embodiments, $y_1$ is 0. In some embodiments, the block copolymer of Formula (I) has the structure of Formula (Ia), or a pharmaceutically acceptable salt, solvate, or hydrate thereof:

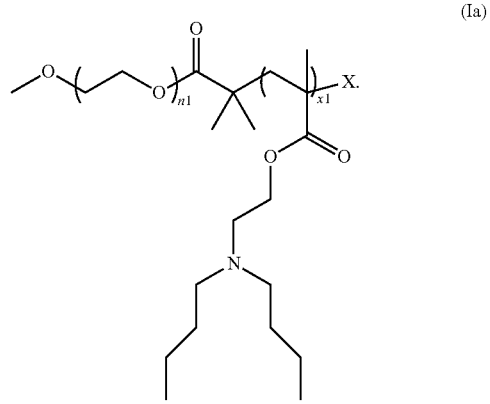

(Ia)

In some embodiments $n_1$ is an integer from 60-150 or 100-140. In some embodiments, $n_1$ is 100-140. In some embodiments, $x_1$ is an integer from 50-200, 60-160, or 90-140. In some embodiments, $x_1$ is an integer from 90-140. In some embodiments, X is a halogen. In some embodiments, X is —Br.

In some embodiments, the therapeutic agent is a monocarboxylate transporter inhibitor. In some embodiments, the therapeutic agent is a monocarboxylate transporter 1 (MCT 1) inhibitor. In some embodiments, the therapeutic agent is a monocarboxylate transport 4 (MCT 4) inhibitor. In some embodiments, the therapeutic agent is selected from α-cyanocinnamate derivatives, stilbene disulfonates such as DIDS (α-cyano-4-hydroxycinnamate (CHC) 4,4'-diisothiocyanostilbene-2,2'-disulfonate), coumarin derivatives, pteridine derivatives, a bioflavonoid such as quercetin, an organomercurial reagent such as p-chlomercuribenzene sulfonate (pCMBS), phloretin, lonidamide, bindarit, and ACF; or a combination thereof. In some embodiments, the MCT inhibitor is AR-C155858, AR-C122982, AR-C117977, AZD3965, or ACF; or a pharmaceutically acceptable salt, solvate, or hydrate thereof. In some embodiments, the MCT inhibitor is AZD3965, or a pharmaceutically acceptable salt, solvate, or hydrate thereof.

In some embodiments, the micelle has a diameter of less than about 1 μm or less than about 50 nm. In some embodiments, the micelle has diameter of about 25 to about 50 nm.

In another aspect of the invention is a pH responsive composition comprising one or more micelles described herein. In some embodiments, the pH responsive composition has a pH transition point. In some embodiments, the pH transition point is between 4-8, 6-7.5, or 4.5-6.5. In some embodiments, composition has a pH response of less than 0.25 or 0.15 pH units.

In another aspect of the invention is a method for treating cancer in an individual in need thereof, comprising administration of an effective amount of a pH-sensitive micelle composition comprising a chemotherapeutic agent as described herein. In some embodiments, the cancer comprises a solid tumor. In some embodiments, the tumor is of a cancer, wherein the cancer is of the breast, ovarian, prostate, peritoneal metastasis, colorectal, bladder, esophageal, head and neck (HNSSC), lung, brain, kidney, renal, or skin (including melanoma and sarcoma). In some embodiments, the tumor is reduced in size by about 50%, about 60%, about 70%, about 80%, about 90%, or about 95%. In some embodiments, micelle described here is administered with one of more additional therapies. In some embodiments, the additional therapy is a checkpoint inhibitor. In some embodiments, the checkpoint inhibitor is an anti-PD-1 therapy, anati-PD-L1 therapy, or anti-CTLA-4 therapy.

Other objects, features and advantages of the block copolymers, micelle compositions, and methods described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
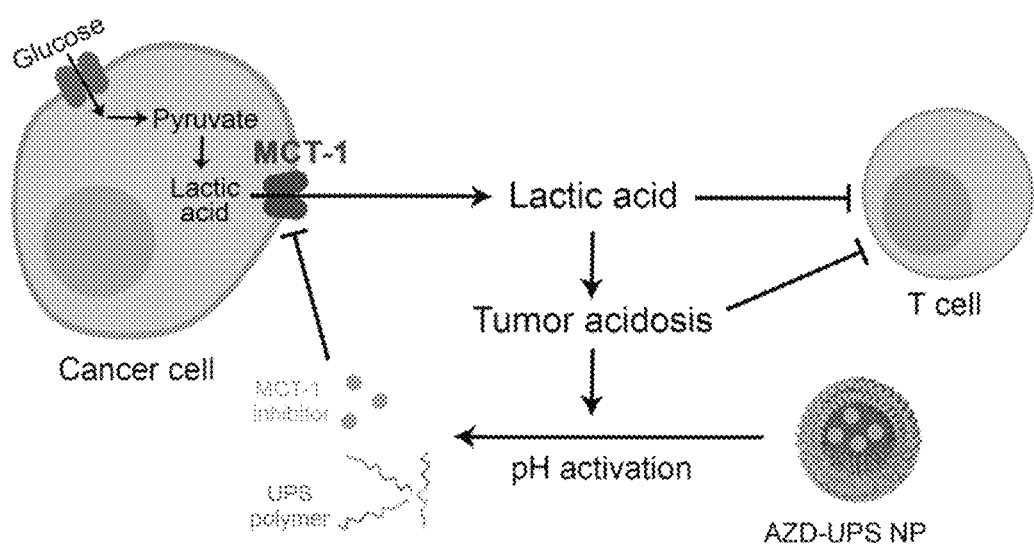
FIG. 1 displays a scheme showing tumor-targeted inhibition of monocarboxylate transporter 1 (MCT 1) by AZD3965-loaded ultra-pH sensitive nanoparticles (AZD-UPS NPs) primes the tumor microenvironment for enhanced T-cell immunity against cancer.

Provided herein are micelle compositions comprising a therapeutic agent. In some embodiments, the micelle comprises a diblock copolymer and a therapeutic agent. In other embodiments provided here in are micelle composition comprising a therapeutic agent.

I. Micelles

One or more block copolymers described herein may be used to form a pH-sensitive micelle. In some embodiments, a composition comprises a single type of micelle. In some embodiments, two or more different types of micelles may be combined to form a mixed-micelle composition. In some embodiments, the micelle comprises one or more block copolymer that non-covalently encapsulates a therapeutic agent.

In certain embodiments provided herein is a micelle, comprising:
(i) a block copolymer, or a pharmaceutically acceptable salt, solvate, or hydrate thereof, the block copolymer comprising:
a hydrophilic polymer segment (Ia):

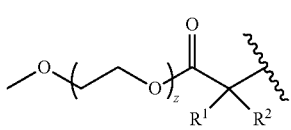

wherein $n_1$ is an integer from 10-200; and
a hydrophobic polymer segment (Ib) covalently bound to the hydrophilic polymer segment (I):

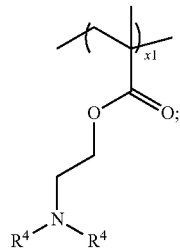

wherein x1 is an integer from 20-300; PG
wherein:
$R^1$ and $R^2$ are each independently hydrogen or an optionally substituted $C_1$-$C_6$ alkyl;
$R^3$ and $R^4$ are each independently an optionally substituted $C_1$-$C_6$ alkyl, $C_3$-$C_{10}$ cycloalkyl or aryl;
or $R^3$ and $R^4$ are taken together with the corresponding nitrogen to which they are attached form an optionally substituted 5 to 7-membered ring; and
(ii) a therapeutic agent encapsulated by the block copolymer, wherein the therapeutic agent is a monocarboxylate transport inhibitor.

In certain embodiments provided herein is a micelle, comprising:
(i) a block copolymer of Formula (I), or a pharmaceutically acceptable salt, solvate, or hydrate thereof:

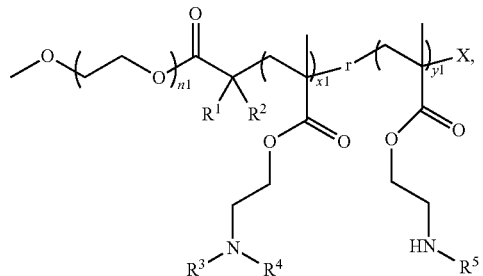

wherein:
$n_1$ is an integer from 10-200;
$x_1$ is an integer from 20-300;
$y_1$ is an integer from 0-10;
X is a halogen, —OH, or —C(O)OH;
$R^1$ and $R^2$ are each independently hydrogen or optionally substituted $C_1$-$C_6$ alkyl;
$R^3$ and $R^4$ are each independently an optionally substituted $C_1$-$C_6$ alkyl, $C_3$-$C_{10}$ cycloalkyl or aryl;
or $R^3$ and $R^4$ are taken together with the corresponding nitrogen to which they are attached form an optionally substituted 5 to 7-membered ring;
$R^5$ is hydrogen or a fluorescent dye; and
(ii) a therapeutic agent encapsulated by the block copolymer, wherein the therapeutic agent is a monocarboxylate transport inhibitor.

In certain embodiments, provided herein is a micelle, comprising:
(i) a block copolymer of Formula (II), or a pharmaceutically acceptable salt, solvate, hydrate, or isotopic variant thereof:

Formula (II)

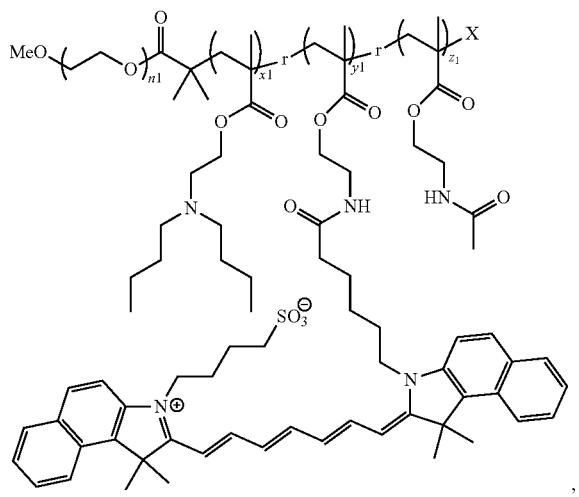

wherein:
$X^1$ is a halogen, —OH, or —(O)OH;
n is 90-140;
$x_1$ is 50-200;
$y_1$ is 0-3; and
$z_1$ is 0-3.
and (ii) a therapeutic agent encapsulated by the block copolymer, wherein the therapeutic agent is a monocarboxylate transport inhibitor.

(i) Block Copolymers

In some embodiments, the micelle comprises a block copolymer of Formula (I), or a pharmaceutically acceptable, salt, solvate, or hydrate thereof.

In some embodiments of Formula (I), $R^1$ and $R^2$ are each independently an optionally substituted $C_1$-$C_6$ alkyl. In some embodiments, $R^1$ and $R^2$ are each independently —$CH_3$, —$CH_2CH_3$, —$CH_2CH_2CH_3$, or —$CH_2CH_2CH_2CH_3$. In some embodiments, $R^1$ and $R^2$ are each independently —$CH_3$. In some embodiments, $R^1$ and $R^2$ are each independently hydrogen.

In some embodiments of Formula (I), the $R^3$ and $R^4$ are each independently an optionally substituted $C_1$-$C_6$ alkyl. In some embodiments, the alkyl is a straight chain or a branch alkyl. In some embodiments, the alkyl is a straight chain alkyl. In some embodiments, $R^3$ and $R^4$ are each independently —$CH_2CH_3$, —$CH_2CH_2CH_3$, or —$CH_2CH_2CH_2CH_3$. In some embodiments, $R^3$ and $R^4$ are each independently —$CH_2CH_2CH_2CH_3$.

In some embodiments, the alkyl is a branched alkyl. In some embodiments, $R^3$ and $R^4$ are each independently —$CH(CH_3)_2$ or —$CH(CH_3)CH_2CH_3$. In some embodiments, $R^3$ and $R^4$ are each independently —$CH(CH_3)_2$.

In some embodiments of the block copolymer of Formula (I), $R^3$ and $R^4$ are each independently an optionally substituted $C_3$-$C_{10}$ cycloalkyl or aryl. In some embodiments, $R^3$ and $R^4$ are each independently an optionally substituted cyclopropyl, cyclobutyl, cyclopentyl, cyclohexyl, or cycloheptyl. In some embodiments, $R^3$ and $R^4$ are each independently an optionally substituted phenyl.

In some embodiments of the block copolymer of Formula (I), $R^3$ and $R^4$ are taken together with the corresponding nitrogen to which they are attached form an optionally substituted 5 to 7-membered ring. In some embodiments, $R^3$ and $R^4$ taken together are —$CH_2(CH_2)_2CH_2$—, —$CH_2(CH_2)_3CH_2$—, or —$CH_2(CH_2)_4CH_2$—. In some embodiments, $R^3$ and $R^4$ taken together are —$CH_2(CH_2)_2CH_2$—. In some embodiments, $R^3$ and $R^4$ taken together are —$CH_2(CH_2)_3CH_2$—. In some embodiments, $R^3$ and $R^4$ taken together are —$CH_2(CH_2)_4CH_2$—.

In some embodiments of the block copolymer of Formula (I), each $R^5$ is independently a fluorescent dye. In some embodiments, each $R^5$ is independently hydrogen. In some embodiments, the fluorescent dye is an indocyanine green dye or analog thereof.

In some embodiments, the block copolymer of Formula (I) has the structure of Formula (Ia), or a pharmaceutically acceptable salt, solvate, or hydrate thereof:

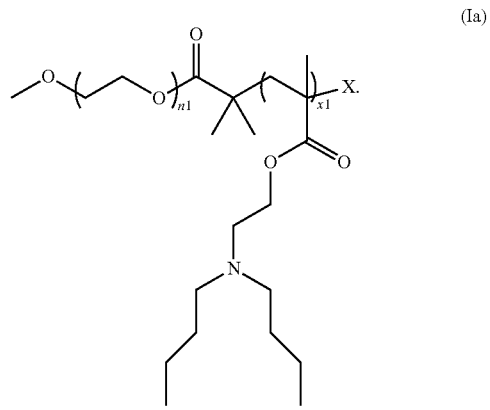

(Ia)

In some embodiments, the block copolymer is a diblock copolymer. In some embodiments, the block copolymer comprises a hydrophilic polymer segment. In some embodiments, the hydrophilic polymer segment comprises poly (ethylene oxide) (PEO). In some embodiments, the polymer is about 2 kD to about 10 kD in size. In some embodiments, the polymer is about 2 kD to about 5 kD in size. In some embodiments, the polymer is about 3 kD to about 8 kD in size. In some embodiments, the polymer is about 4 kD to about 6 kD in size. In some embodiments, the polymer is about 5 kD in size.

In some embodiments, each $n_1$ and $n_2$ is independently an integer from 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-99, 100-109, 110-119, 120-129, 130-139, 140-149, 150-159, 160-169, 170-179, 180-189, 190-199 or any range derivable therein. In some embodiments, each $n_1$ and $n_2$ is independently an integer from 60-150, 100-140, or 110-120. In some embodiments, each $n_1$ and $n_2$ is independently 100-140.

In some embodiments, the block copolymer comprises a hydrophobic polymer segment. In some embodiments, the hydrophobic polymer segment is selected from:

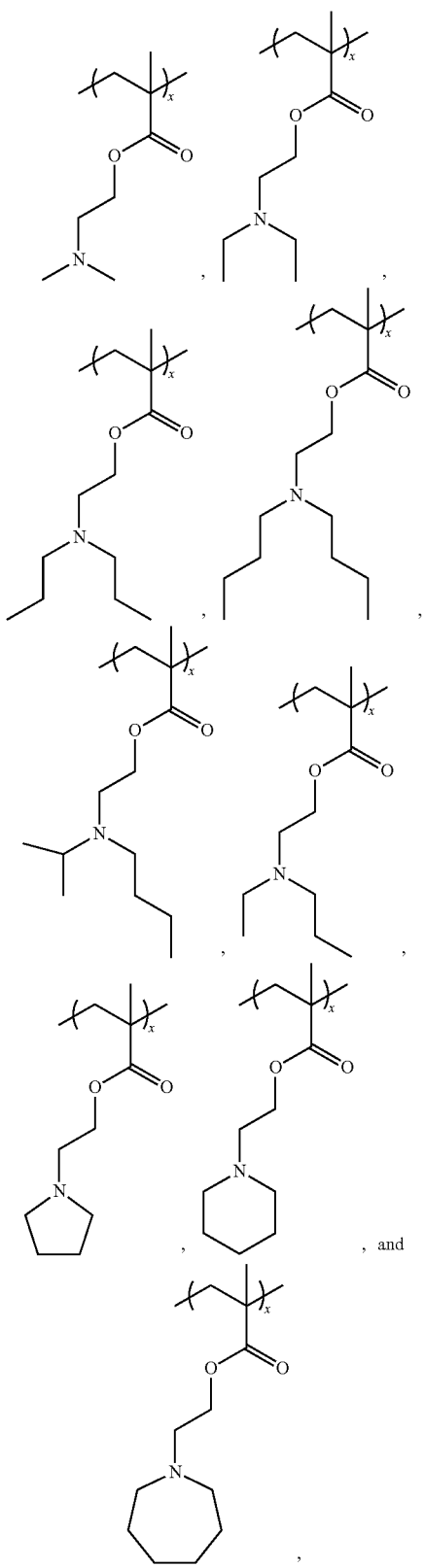

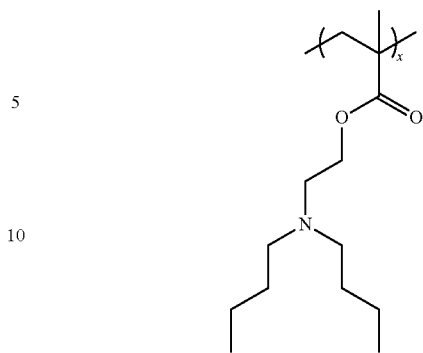

wherein x is about 20-300 in total.

In some embodiments, the hydrophobic segment comprises a dibutyl amine. In some embodiments, the hydrophobic segment comprises In some embodiments, $x_1$, is an integer 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-99, 100-109, 110-119, 120-129, 130-139, 140-149, 150-159, 160-169, 170-179, 180-189, 190-199 or any range derivable therein. In some embodiments, $x_1$ is an integer from 50-200, 60-160, or 90-140. In some embodiments, $x_1$ is 90-140.

In some embodiments, $y_1$ is an integer from 1-9, 1-8, 1-7, 1-6, 1-5, 1-4, or 1-3, or any range derivable therein. In some embodiments, $y_1$ is 1, 2, 3, 4, 5, 6, 7, 8, 9, or 10. In some embodiments, $y_1$ is 0.

In some embodiments, X is a terminal group. In some embodiments, the terminal capping group is the product of an atom transfer radical polymerization (ATRP) reaction. For example, the terminal capping group may be a halogen, such as —Br, when atom transfer radical polymerization (ATRP) is used. In some embodiments, X is Br. In some embodiments, X is independently —OH. In some embodiments, each X is an acid. In some embodiments, X is —C(O)OH. In some embodiments, X is H. The end group may optionally be further modified following polymerization with an appropriate moiety.

In certain embodiments, the block copolymer comprises a fluorescent dye conjugated through an amine. In some embodiments, the fluorescent dye is a cyanine dye or a derivative thereof. In some embodiments, the fluorescent dye is indocyanine green (ICG) or a derivative thereof. Indocyanine green (ICG) is used in medical diagnostics. In some embodiments, the structure of ICG or derivative thereof is:

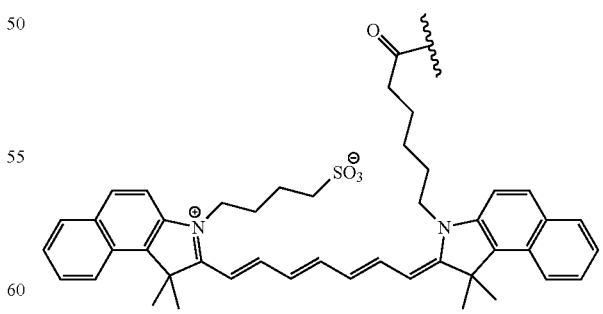

(ii) Therapeutic Agents

Monocarboxylate transport inhibitors are implicated in production of lactic acid linked to tumor cell metabolism and growth (Payen et al, *Molecular Metabolism*, 2019, 33, 46-66). In some embodiments, the therapeutic agent is a monocarboxylate transporter (MCT) inhibitor. In some embodiments, the monocarboxylate transport inhibitor is a MCT 1, MCT 2, MCT 3, or MCT 4 inhibitor. In some embodiments, the therapeutic agent is a MCT 1 inhibitor or a MCT 4 inhibitor.

In some embodiments, the monocarboxylate transport (MCT) inhibitor is selected from α-cyanocinnamate derivatives, stilbene disulfonates such as DIDS (α-cyano-4-hydroxycinnamate (CHC) 4,4'-diisothiocyanostilbene-2,2'-disulfonate), coumarin derivatives, pyrrolopyridazinone or thienopyrimidine dione, pteridine or a pteridine derivative, a bioflavonoid such as quercetin, an organomercurial reagent such as p-chlomercuribenzene sulfonate (pCMBS), phloretin, lonidamide, bindarit, (2-[(1-benzyl-1H-indazol-3-yl)methoxy]-2-methylpropanoic acid; or a combination thereof. In some embodiments, the monocarboxylate transport (MCT) inhibitor is selected from AR-C155858, AR-C122982, AR-C117977, and AZD3965.

In some embodiments, the monocarboxylate transport (MCT) inhibitor is a pyrrolopyridazinone or thienopyrimidine dione. In some embodiments, the pyrrolopyridazinone or thienopyrimidine dione is Compound 1 or 2:

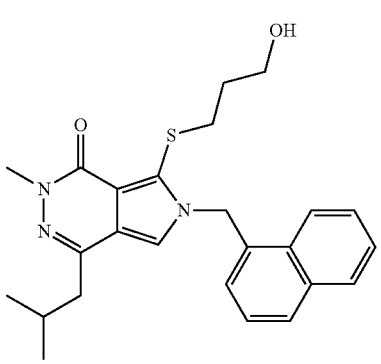

(1)

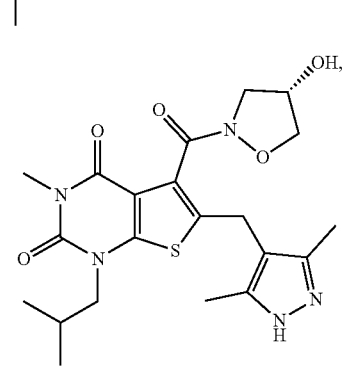

(2)

or a pharmaceutically acceptable salt, solvate, or hydrate thereof.

In some embodiments, the monocarboxylate transport (MCT) inhibitor is pteridine or a derivative thereof. In some embodiments, pteridine has the structure:

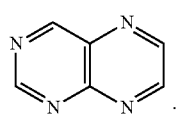

In some embodiments, the monocarboxylate transport (MCT) inhibitor is compound having the structure of Formula IIa, IIb, IIIa, or IIIb, or a pharmaceutically acceptable salt, solvate, or hydrate thereof:

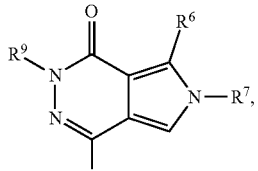

(IIa)

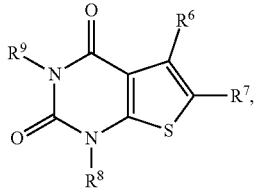

(IIb)

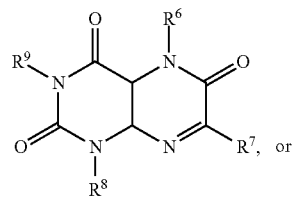

(IIIa)

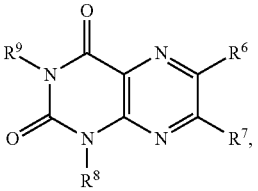

(IIIb)

wherein
$R^6$ is an optionally substituted $C_1$-$C_6$ alkylene, $C_1$-$C_6$ alkenylene, $C_1$-$C_6$ heteroalkylene, —S(O)$_p$R$^{11}$, —C(O)NR$^{10}$R$^{11}$, —C(O)R$^{11}$, —C(O)$_2$R$^{11}$, aryl, or heteroaryl;
$R^{10}$ is hydrogen, or an optionally substituted $C_1$-$C_6$ alkyl, or $C_1$-$C_6$ heteroalkyl;
$R^{11}$ is hydrogen, or an optionally substituted $C_1$-$C_6$ alkyl, $C_1$-$C_6$ heteroalkyl, or 5 to 6-membered heterocycloalkyl ring;
p is 1 or 2;
$R^7$ is optionally substituted $C_1$-$C_6$ alkyl, —$C_1$-$C_3$ alkyl (aryl), or —$C_1$-$C_3$ alkyl(heteroaryl);
$R^8$ and $R^9$ are each independently an optionally substituted $C_1$-$C_6$ alkyl; and
wherein each alkyl, heteroalkyl, heterocycle, aryl, and heteroaryl is optionally substituted with one, two, or three halogen, $C_1$-$C_3$ alkyl, $C_1$-$C_3$ haloalkyl or —OH.

In some embodiments, the monocarboxylate transport (MCT) inhibitor is a compound having the structure of IIa or IIb, or a pharmaceutically acceptable salt, solvate, or hydrate thereof. In some embodiments, the monocarboxylate transport (MCT) inhibitor is a compound having the structure of Formula IIIa or IIIb, or a pharmaceutically acceptable salt, solvate, or hydrate thereof.

In some embodiments, $R^6$ is an optionally substituted $C_1$-$C_6$ alkylene or $C_1$-$C_6$ heteroalkylene. In some embodiments, $R^6$ is —CH$_2$(CH$_2$)$_m$, —CH$_2$(CH$_2$)$_m$—OH, or —CH$_2$(CH$_2$)$_m$—OH, wherein m is an integer from 3-6.

In some embodiments, $R^6$ is —C(O)NR$^{10}$R$^{11}$, —C(O)R$^{11}$ or —C(O)$_2$R$^{11}$, wherein $R^{10}$ and $R^{11}$ are each independently hydrogen or an optionally substituted $C_1$-$C_6$ alkyl. In some embodiments, $R^{10}$ is hydrogen. In some embodiments, $R^{11}$ is an optionally substituted $C_1$-$C_6$ alkyl, optionally substituted with one, two, or three halogen, $C_1$-$C_3$ alkyl, $C_1$-$C_3$ haloalkyl, or —OH.

In some embodiments, $R^6$ is —C(O)$R^{11}$, wherein $R^{11}$ is an optionally substituted 5 to 6-membered heterocycloalkyl. In some embodiments, $R^{11}$ is an optionally substituted 5-membered heterocycloalkyl ring optionally substituted with one, two, or three $C_1$-$C_3$ alkyl or $C_1$-$C_3$ haloalkyl.

In some embodiments, $R^6$ is an optionally substituted aryl or heteroaryl. In some embodiments, the heteroaryl is a 5 or 6-membered heteroaryl. In some embodiments, the heteroaryl is a 5-membered heteroaryl.

In some embodiments, $R^7$ is an optionally substituted —$C_1$-$C_3$ alkyl(aryl). In some embodiments, $R^7$ is —CH$_2$-phenyl or —CH$_2$-naphthyl. In some embodiments, $R^7$ is an optionally substituted $C_1$-$C_3$ alkyl(heteroaryl). In some embodiments, the heteroaryl is 5 or 6-membered heteroaryl. In some embodiments, the $R^7$ is an optionally substituted —CH$_2$-(5-membered heteroaryl), optionally substituted with one or two $C_1$-$C_3$ alkyl or $C_1$-$C_3$ haloalkyl.

In some embodiments, $R^8$ and $R^9$ are each independently methyl, ethyl, propyl, or butyl. In some embodiments, $R^8$ is methyl or ethyl. In some embodiments, $R^9$ is isopropyl, isobutyl, sec-butyl, or tert-butyl. In some embodiments, $R^8$ is methyl and $R^9$ is isopropyl or isobutyl.

In some embodiments, the monocarboxylate transport (MCT) inhibitor is a compound selected from:

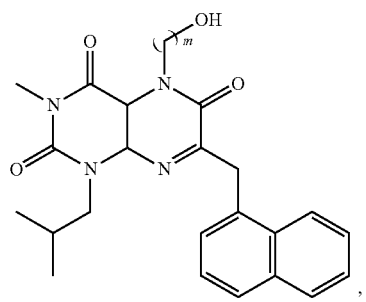

(1)

wherein m is an integer from 3-6;

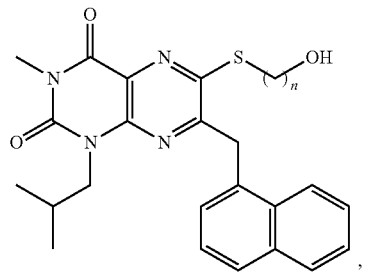

(2)

wherein n is an integer from 2-4;

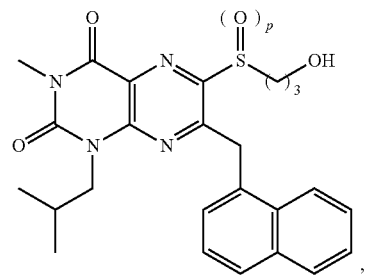

(3)

wherein p is 1 or 2;

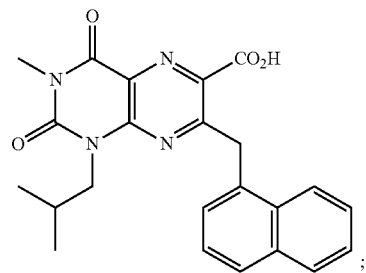

(4)

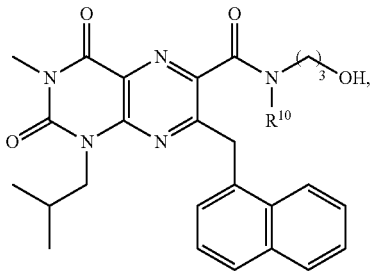

(5)

wherein $R^{10}$ is hydrogen or methyl;

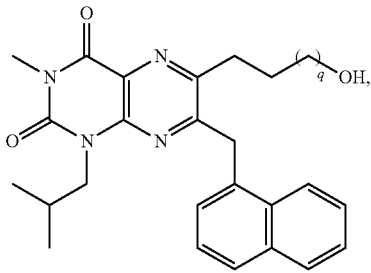

(6)

wherein q is an integer from 2-4;

(7) 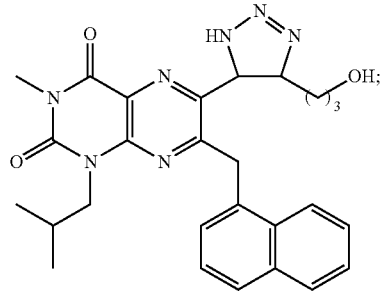
(8) 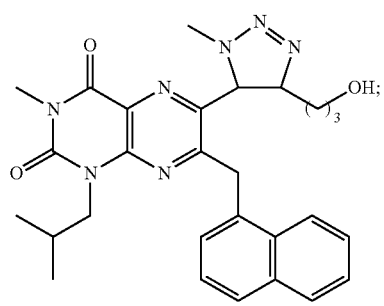
(9) 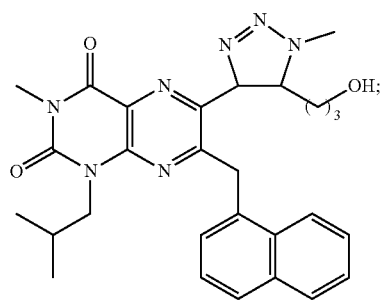
(10) 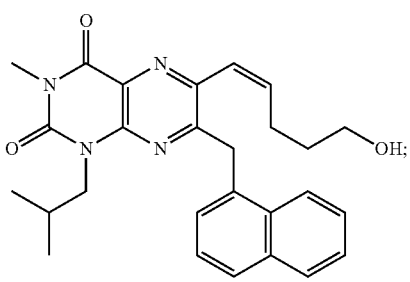
(11) 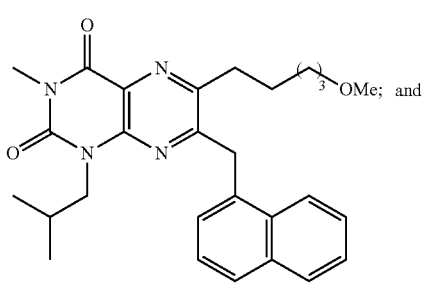
(12) 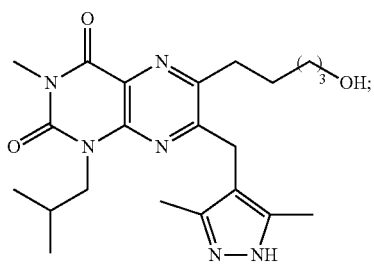
or a pharmaceutically acceptable salt, solvate, or hydrate thereof.
In some embodiments, the monocarboxylate transport (MCT) inhibitor is:
(AR-C122982)
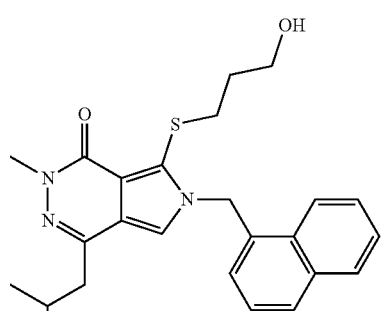
(AR-C155858)
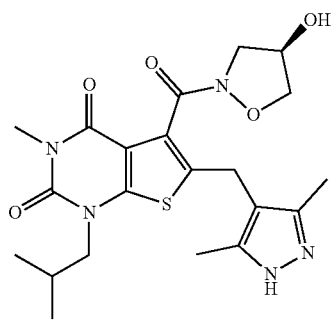
(AR-C177977)
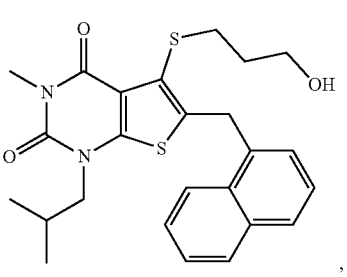

-continued

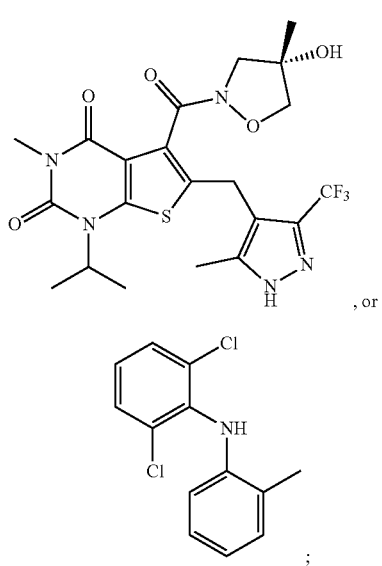

(AZD3965)

, or (ACF)

or a pharmaceutically acceptable salt, solvate, or hydrate thereof. In some embodiments, the MCT inhibitor is AR-C122982, or a pharmaceutically acceptable salt, solvate, or hydrate thereof. In some embodiments, the MCT inhibitor is AR-C155858, or a pharmaceutically acceptable salt, solvate, or hydrate thereof. In some embodiments, the MCT inhibitor is AR-C177977, or a pharmaceutically acceptable salt, solvate, or hydrate thereof. In some embodiments, the MCT inhibitor is ACF, or a pharmaceutically acceptable salt or solvate thereof.

In some embodiments, the therapeutic agent is a monocarboxylate transport inhibitor. In some embodiments, the MCT inhibitor is AZD3965, or a pharmaceutically acceptable salt, solvate, or hydrate thereof:

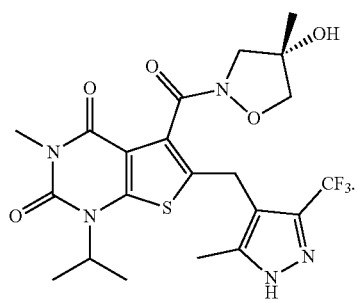 [SMILES: Cc1[nH]nc(C(F)(F)F)c1Cc1sc2c(c1C(=O)N1C[C@](C)(O)CO1)c(=O)n(C)c(=O)n2C(C)C]

In some embodiments, the micelle comprises one or more different types of block copolymer components from various unimers. In some embodiments, the therapeutic agent is encapsulated within the micelle. In some embodiments, the therapeutic agent is non-covalently encapsulated by the micelle comprising the block copolymer. The therapeutic agent may be incorporated into the micelles using methods known in the art.

The use of micelles in cancer therapy may enhance anti-tumor efficacy and reduce toxicity to healthy tissues, in part due to the size of the micelles. While small molecules such as certain chemotherapeutic agents can enter both normal and tumor tissues, non-targeted micelle nanoparticles may preferentially cross leaky tumor vasculature. The size of the micelles will typically be in the nanometer scale (i.e., between about 1 nm and 1 μm in diameter). In some embodiments, the micelle has a diameter of less than about 1 μm or less then about 50 nm. In some embodiments, the micelle has a diameter of less then about 1 μm. In some embodiments, the micelle has a diameter of less then about 50 nm. In some embodiments, the micelle has a size of about 10 to about 200 nm. In some embodiments, the micelle has a size of about 20 to about 100 nm. In some embodiments, the micelle has a size of about 30 to about 50 nm.

II. pH Responsive Compositions

In another aspect presented herein, are pH responsive compositions. The pH responsive compositions disclosed herein, comprise one or more pH-responsive micelles and/or nanoparticles that comprise block copolymers and a therapeutic agent. Each block copolymer comprises a hydrophilic polymer segment and a hydrophobic polymer segment wherein the hydrophobic polymer segment comprises an ionizable amine group to render pH sensitivity. This pH sensitivity is exploited to provide compositions suitable as drug-conjugate therapeutics.

The micelles may have different pH transition values within physiological range, in order to target specific cells or microenvironments. In some embodiments, the micelle has a pH transition value of about 5 to about 8. In some embodiments, the micelle has a pH transition value of about 5 to about 6. In some embodiments, the micelle has a pH transition value of about 6 to about 7. In some embodiments, the micelle has a pH transition value of about 7 to about 8. In some embodiments, the micelle has a pH transition value of about 6.3 to about 6.9. In some embodiments, the micelle has a pH transition value of about 5.0 to about 6.2. In some embodiments, the micelle has a pH transition value of about 5.9 to about 6.2. In some embodiments, the micelle has a pH transition value of about 5.0 to about 5.5. In some embodiments, the pH transition point is 4.8, 4.9, 5.0, 5.1, 5.2, 5.3, 5.4, or 5.5.

The pH-sensitive micelle compositions of the invention may advantageously have a narrow pH transition range, in contrast to other pH sensitive compositions in which the pH response is very broad (i.e. 2 pH units). This pH transition is the transition point at which the micelle dissociates, releasing the payload or activating the photophore (i.e., an indocyanine green dye). In some embodiments, the micelles have a pH transition range of less than about 1 pH unit. In various embodiments, the micelles have a pH transition range of less than about 0.9, less than about 0.8, less than about 0.7, less than about 0.6, less than about 0.5, less than about 0.4, less than about 0.3, less than about 0.2, less than about 0.1 pH unit. In some embodiments, the micelles have a pH transition range of less than about 0.5 pH unit. In some embodiments, the micelles have a pH transition range of less than about 0.25 pH unit. The narrow pH transition range advantageously provides a sharper pH response that can result in complete turn-on of the fluorophores or release the therapeutic payload with subtle changes of pH.

In some embodiments, the pH responsive compositions have an emission spectrum. In some embodiments, the emission spectrum is from 600-800 nm. In some embodiments, the emission spectrum is from 700-800 nm.

III. Methods of Use

Aerobic glycolysis, known as the Warburg effect, in which cancer cells preferentially uptake glucose and convert it into lactic acid or other acids, occurs in all solid cancers. Lactic acid or other acids preferentially accumulates in the extracellular space due to monocarboxylate transporters or other transporters. The resulting acidification of the extracellular space promotes remodeling of the extracellular matrix for further tumor invasion and metastasis.

Some embodiments provided herein describe compounds that form micelles at physiologic pH (7.35-7.45). In some embodiments, the compounds described herein are non-covalently conjugated to a therapeutic agent. In some embodiments, the micelle has a molecular weight of greater than $2\times10^7$ Daltons. In some embodiments, the micelle has a molecular weight of ~$2.7\times10^7$ Daltons. In some embodiments, the therapeutic agents are sequestered within the micelle core at physiologic pH (7.35-7.45) (e.g., during blood circulation). In some embodiments, when the micelle encounters an acidic environment (e.g., tumor tissues), the micelles dissociate into individual compounds with an average molecular weight of about $3.7\times10^4$ Daltons, allowing the release of the therapeutic agent. In some embodiments, the micelle dissociates at a pH below the pH transition point (e.g. the acidic state of tumor microenvironment).

In some embodiments, the therapeutic agent may be incorporated into the interior of the micelles. Specific pH conditions (e.g. acidic pH present in tumors and endocytic compartments) may lead to rapid protonation and dissociation of micelles into unimers, thereby releasing the therapeutic agent (e.g. a drug). In some embodiments, the micelle provides stable drug encapsulation at physiological pH (pH 7.4), but can quickly release the drug in acidic environments.

In some instances, the pH-sensitive micelle compositions described herein have a narrow pH transition range. In some embodiments, the micelles described herein have a pH transition range ($\Delta pH_{10-90\%}$) of less than 1 pH unit. In various embodiments, the micelles have a pH transition range of less than about 0.9, less than about 0.8, less than about 0.7, less than about 0.6, less than about 0.5, less than about 0.4, less than about 0.3, less than about 0.2, less than about 0.1 pH unit. In some embodiments, the micelles have a pH transition range of less than about 0.5 pH unit. In some embodiments, the pH transition range is less than 0.25 pH units. In some embodiments, the pH transition range is less than 0.15 pH units. A sharp transition point allows the micelles to dissociate with the acidic tumor microenvironment.

These micelles may be used as drug-delivery agents. Micelles comprising a drug may be used to treat e.g. cancers, or other diseases wherein the drug may be delivered to the appropriate location due to localized pH differences (e.g. a pH different from physiological pH (7.4)). In some embodiments, the disorder treated is a cancer. In some embodiments, the cancer comprises a solid tumor. In some embodiments, the tumor is a secondary tumor from metastasis of a primary tumor(s). In some embodiments, the drug-delivery may be to a lymph node or to a pleural surface.

In some embodiments of the methods disclosed herein, the tumor is from a cancer. In some embodiments, the cancer is breast cancer, head and neck squamous cell carcinoma (NHSCC), lung cancer, ovarian cancer, prostate cancer, bladder cancer, urethral cancer, esophageal cancer, colorectal cancer, peritoneal metastasis, renal cancer, or brain, skin (including melanoma and sarcoma). In some embodiments, the cancer is breast cancer, head and neck squamous cell carcinoma (NHSCC), esophageal cancer, colorectal cancer, or renal cancer.

In some embodiments, the tumor is reduced by about 5%, about 10%, about 15%, about 25%, about 30%, about 40%, about 50%, about 60%, about 70%, about 80%, or about 90%. In some embodiments, the tumor is reduced by about 50%. In some embodiments, the tumor is reduced by about 60%. In some embodiments, the tumor is reduced by about 70%. In some embodiments, the tumor is reduced by about 75%. In some embodiments, the tumor is reduced by about 80%. In some embodiments, the tumor is reduced by about 85%. In some embodiments, the tumor is reduced by about 90%. In some embodiments, the tumor is reduced by about 95%. In some embodiments, the tumor is reduced by about 99%.

IV. Combination Therapy

In another aspect, the micelles comprising a block copolymer of Formula (I), or a pharmaceutically acceptable salt, solvate, or hydrate thereof; and a therapeutic agent further comprise the administration of one or more additional therapies. In some embodiments, the additional therapy is checkpoint inhibitor. Checkpoint inhibitor therapy is a form of cancer immunotherapy. The therapy targets immune checkpoints, key regulators of the immune system that when stimulated can dampen the immune response to an immunologic stimulus. Some cancers can protect themselves from attack by stimulating immune checkpoint targets. Checkpoint therapy can block inhibitory checkpoints, restoring immune system function. Examples of checkpoint proteins found on T-cells or cancer cells include PD-1/PD-L1 and CTLA-4/B7-1B7-2. Some immune checkpoint inhibitors are used to treat cancer.

PD-1 inhibitors and PD-L1 inhibitors are a group of checkpoint inhibitor anticancer drugs that block the activity of PD-1 and PDL1 immune checkpoint proteins present on the surface of cells. Immune checkpoint inhibitors are emerging as a front-line treatment for several types of cancer.

In some embodiments, the additional therapy is a checkpoint inhibitor. In some embodiments, the checkpoint inhibitor is an anti-PD-1 therapy, anati-PD-L1 therapy, or anti-CTLA-4 therapy. In some embodiments, the checkpoint inhibitor is an anti-PD-1 therapy.

In some embodiments, the additional therapy is selected from Pembrolizumab (Keytruda), Nivolumab (Opdivo), Cemiplimab (Libtayo), and Durvalumab (Imfinzi); or any combination thereof. In some embodiments, the additional therapy is Pembrolizumab or Keytruda. In some embodiments, the additional therapy is Nivolumab or Opdivo. In some embodiments, the additional therapy is Durvalumab or Imfinzi. In some embodiments, the additional therapy is Cemiptimab or Libtayo.

The additional therapy may be administered concurrently or sequentially with the pH responsive composition described herein.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl, ethyl, s-butyl, or 1-ethyl-propyl. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$OMe, —OCH$_2$CH$_2$OMe, or —OCH$_2$CH$_2$OCH$_2$CH$_2$NH$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthalenyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

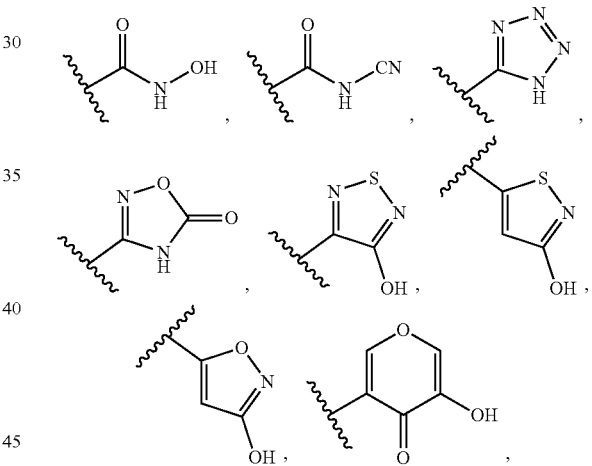

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. In some embodiments, a cycloalkyl is a $C_3$-$C_6$ cycloalkyl. In some embodiments, a cycloalkyl is a 3- to 6-membered cycloalkyl. Representative cycloalkyls include, but are not limited to, cycloakyls having from three to ten carbon atoms, from three to eight carbon atoms, from three to six carbon atoms, or from three to five carbon atoms. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. Polycyclic radicals include, for example, adamantyl, norbornyl, decalinyl, and 3,4-dihydronaphthalen-1(2H)-one.

Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 13 carbon atoms and from one to 6 heteroatoms selected from the group consisting of nitrogen, oxygen, and sulfur. In some embodiments, the heterocycloalkyl is a $C_2$-$C_7$ heterocycloalkyl. In some embodiments, the heterocycloalkyl is a $C_2$-$C_6$ heterocycloalkyl. In some embodiments, the heterocycloalkyl is a $C_2$-$C_5$ heterocycloalkyl. In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 3- to 5-membered heterocycloalkyl. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to an aryl group that includes one or more ring heteroatoms selected from nitrogen, oxygen and sulfur. The heteroaryl is monocyclic or bicyclic. In some embodiments, the heteroaryl is a 5- or 6-membered heteroaryl. In some embodiments, the heteroaryl is a 5-membered heteroaryl. In some embodiments, the heteroaryl is a 6-membered heteroaryl. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g., —$NH_2$, —NHR, —N(R)$_2$), and the protected derivatives thereof. In some embodiments, optional substituents are independently selected from alkyl, alkoxy, haloalkyl, cycloalkyl, halogen, —CN, —$NH_2$, —NH(CH$_3$), —N(CH$_3$)$_2$, —OH, —$CO_2H$, and —$CO_2$alkyl. In some embodiments, optional substituents are independently selected from fluoro, chloro, bromo, iodo, —CH$_3$, —CH$_2$CH$_3$, —CF$_3$, —OCH$_3$, and —OCF$_3$. In some embodiments, optional substituents are independently selected from fluoro, chloro, —CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

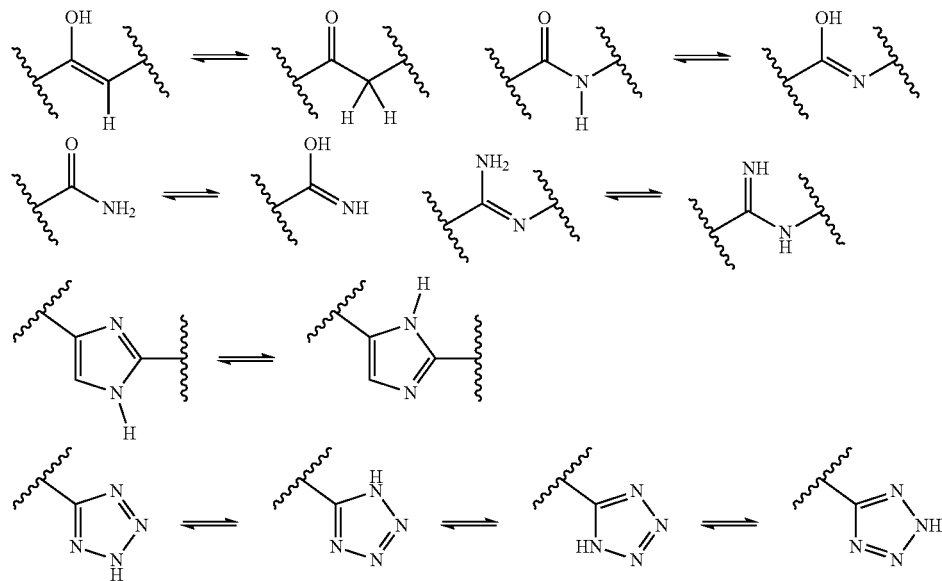

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

"Pharmaceutically acceptable," as used herein, refers a material, such as a carrier or diluent, which does not abrogate the biological activity or properties of the block copolymer, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zurich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a block copolymer with an acid. In some embodiments, the block copolymer of Formula (A) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (-L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (-L); salicylic acid; sebacic acid; stearic acid; succinic acid; sulfuric acid; tartaric acid (+L); thiocyanic acid; toluenesulfonic acid (p); and undecylenic acid.

In some embodiments, a block copolymer of Formula (A) is prepared as a chloride salt, sulfate salt, bromide salt, mesylate salt, maleate salt, citrate salt or phosphate salt.

In some embodiments, pharmaceutically acceptable salts are obtained by reacting a block copolymer of Formula (A) with a base. In some embodiments, the block copolymer of Formula (A) is acidic and is reacted with a base. In such situations, an acidic proton of the block copolymer of Formula (A) is replaced by a metal ion, e.g., lithium, sodium, potassium, magnesium, calcium, or an aluminum ion. In some cases, block copolymers described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, block copolymers described herein form salts with amino acids such as, but not limited to, arginine, lysine, and the like. Acceptable inorganic bases used to form salts with block copolymers that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the block copolymers provided herein are prepared as a sodium salt, calcium salt, potassium salt, magnesium salt, melamine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of block copolymers having the structure of Formula (A), as well as active metabolites of these compounds having the same type of activity.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

As used herein, "pH responsive system," "pH responsive composition," "micelle," "pH-responsive micelle," "pH-sensitive micelle," "pH-activatable micelle" and "pH-activatable micellar (pHAM) nanoparticle" are used interchangeably herein to indicate a micelle comprising one or more compounds, which disassociates depending on the pH (e.g., above or below a certain pH). As a non-limiting example, at a certain pH, the block copolymers of Formula (II) is substantially in micellar form. As the pH changes (e.g., decreases), the micelles begin to disassociate, and as the pH further changes (e.g., further decreases), the block copolymers of Formula (II) is present substantially in disassociated (non-micellar) form.

As used herein, "pH transition range" indicates the pH range over which the micelles disassociate.

As used herein, "pH transition value" (pH) indicates the pH at which half of the micelles are disassociated.

A "nanoprobe" is used herein to indicate a pH-sensitive micelle which comprises an imaging labeling moiety. In some embodiments, the labeling moiety is a fluorescent dye. In some embodiments, the fluorescent dye is indocyanine green dye.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally. In some embodiments, the compositions described herein are administered intravenously.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the standard deviation of error for the device or method being employed to determine the value. Following longstanding patent law, the words "a" and "an," when used in conjunction with the word "comprising" in the claims or specification, denotes one or more, unless specifically noted.

EXAMPLES

Block copolymers and micelles described herein are synthesized using standard synthetic techniques or using methods known in the art.

Unless otherwise indicated, conventional methods of mass spectroscopy, NMR, HPLC, protein chemistry, biochemistry, recombinant DNA techniques and pharmacology are employed.

Block copolymers are prepared using standard organic chemistry techniques such as those described in, for example, March's Advanced Organic Chemistry, 6$^{th}$ Edition, John Wiley and Sons, Inc.

Some abbreviations used herein are as follows:
ATRP Atom transfer radical polymerization
DCM: dichloromethane
DMAP: 4-dimethylaminopyridine
DMF: dimethyl formamide
DMF-DMA: N,N-dimethylformamide dimethyl acetal
DMSO Dimethylsulfoxide
EDCI: 1-ethyl-3-(3-dimethylaminopropyl) carbodiimide
EtOAc: ethyl acetate
EtOH: ethanol
ICG-OSu: indocyanine green succinamide ester
MeOH: methanol
PEG Polyethylene glycol
PMDETA: N,N,N',N'',N''-Pentamethyldiethylenetriamine
CDI carbonyldiimidazole
NHS-Carbonate N-hydroxysuccinimide carbonate
SPDB N-succinimidyl-4-(2-pyridyldithio)butanoate
TEA: triethyl amine
TFA Triflouroracetic acid
Hr Hour(s)
ISR Incurred sample reanalysis
IV Intravenous
kg Kilogram
mg Milligram(s)
mL Milliliters(s)
NP Nanoparticle
µg Microgram(s)
µm Mircon(s)
NC Not calculated
NR Not reported
RAFT Reversible addition-fragmentation chain transfer
UPS Ultra pH-sensitive Suitable PEG polymers may be purchased (for example, from Sigma Aldrich) or may be synthesized according to methods known in the art. In some embodiments, the hydrophilic polymer can be used as an initiator for polymerization of the hydrophobic monomers to form a block copolymer. For example, MPC polymers (e.g. narrowly distributed MPC polymers) can be prepared by atom transfer radical polymerization (ATRP) with commercially available small molecule initiators such as ethyl 2-bromo-2-methylpropanoate (e.g. from Sigma Aldrich). These resulting MPC polymers can be used as macromolecular ATRP initiators to further copolymerize with other monomers to form block polymers can be synthesized using atom transfer radical polymerization (ATRP) or reversible addition-fragmentation chain transfer (RAFT) methods.

Block copolymers of Formula (II) were synthesized using a 5-step process. Steps 1 thru 4 were performed in a controlled manufacturing environment. Intermediate 8 (PDBA) was synthesized by atom transfer radical polymerization (ATRP, Step 4) of 3 (PEG-Br, a macroinitiator), 7 ((dibutylamino)ethyl methacrylate, DBA-MA), and 4 (aminoethylmethylacrylate hydrochloride, AMA-MA). The final step included preparation of the Compound 1 by covalently attaching 8 (the diblock copolymer backbone of PDBA) to 9 (the ICG fluorophore (ICG-OSu)). In step 5, all raw materials, solvents and reagents used are either National Formulary (NF) or United States Pharmacopeia (USP) verified except for intermediate 9 (ICG-OSu) which was sourced as a GMP manufactured material. As a precautionary measure Compound 1 was stored at −80° C.±15° C. and protected from light.

Schemes 1 and 2, provides a process flow chart followed by a detailed description of the manufacturing process.

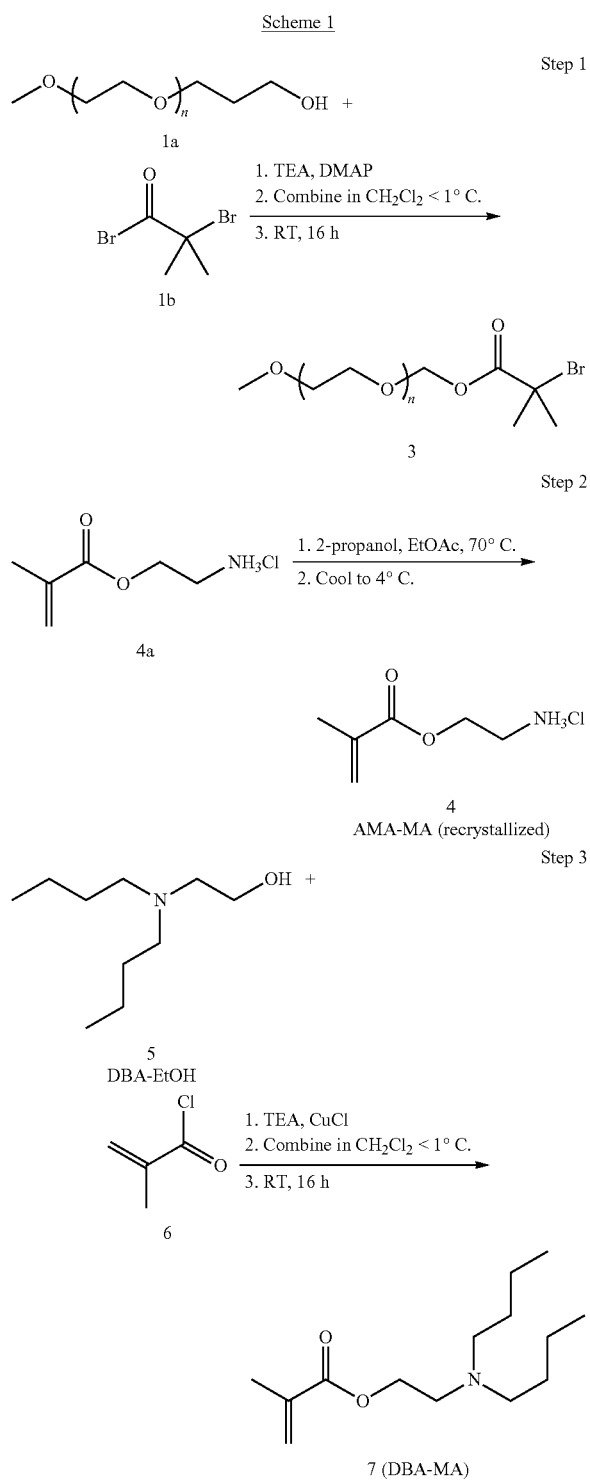

Step 1:

Synthesis:

Poly(ethyleneglycol) methyl ether (PEG-OH) 1a, trimethylamine, 4-(dimethylamino) pyridine (DMAP) in dichloromethane ($CH_2Cl_2$) were cooled in an ice bath. α-Bromoisobutyryl bromide 1b in dichloromethane was then added dropwise to the flask while the flask was maintained in the ice bath. The reaction mixture was allowed to warm to room temperature (RT) and stirred for 16 hrs.

Purification:

The reaction mixture was then added slowly to a beaker containing ~10-fold excess by volume of diethyl ether under stirring to precipitate the crude product 3. The crude product was then filtered and dried in a vacuum oven. The dried, crude 3 was recrystallized from ethanol five times and dried in a vacuum oven to yield the purified 3 (PEG-Br macroinitiator). A typical yield is 40%-70% with a purity of >93% (High-performance liquid chromatography [HPLC] area %).

Step 2:

Recrystallization:

Crude 2-Aminoethylmethacrylate hydrochloride (AMA-MA monomer), 2-propanol 4a and ethyl acetate were combined and heated to 70° C. until the solid was dissolved. The solution was filtered through a pre-heated Buchner funnel containing celite. The filtered solution was allowed to cool to RT and then further cooled to 2-8° C. to crystallize over a period of 8 to 16 hr. The resulting crystalline solids were allowed to warm to RT and were then filtered and washed 3 times with cold ethyl acetate. The isolated crystalline product was dried under vacuum to give purified 4 and stored at −80° C. for use in Step 4. A typical yield is 40%-70% with purity indicated by solubility in a use-test and also a sharp melting point (<3° C.) in the range of 102–124° C.

Step 3:

Synthesis:

2-(Dibutylamino) ethanol (DBA-EtOH, 5), trimethylamine, copper (I) chloride (CuCl) and dichloromethane were combined in a flask and cooled in an ice bath. Methacryloyl chloride 6 was then added dropwise to the flask while maintaining in the ice bath. The reaction mixture was allowed to warm to RT and was stirred for 16 hrs. The reaction mixture was then cooled in an ice bath and filtered. The filtrate was transferred to a separatory funnel and the organic phase was washed twice with saturated aqueous solution of sodium bicarbonate ($NaHCO_3$) followed by one wash with DI water. The organic phase was then dried over anhydrous sodium sulfate ($Na_2SO_4$), filtered and the solvents were removed in vacuo using a rotary evaporator to yield the monomer product 7 as a liquid.

Purification:

Additional CuCl was added as a stabilizer and the product was purified by vacuum distillation. The clear to yellowish distillate 7 (DBA-MA) was transferred to an amber vial and stored at −80° C. for use in Step 4. A typical yield is 30%-60% with a purity of >93% (HPLC area %).

Scheme 2
Step 4
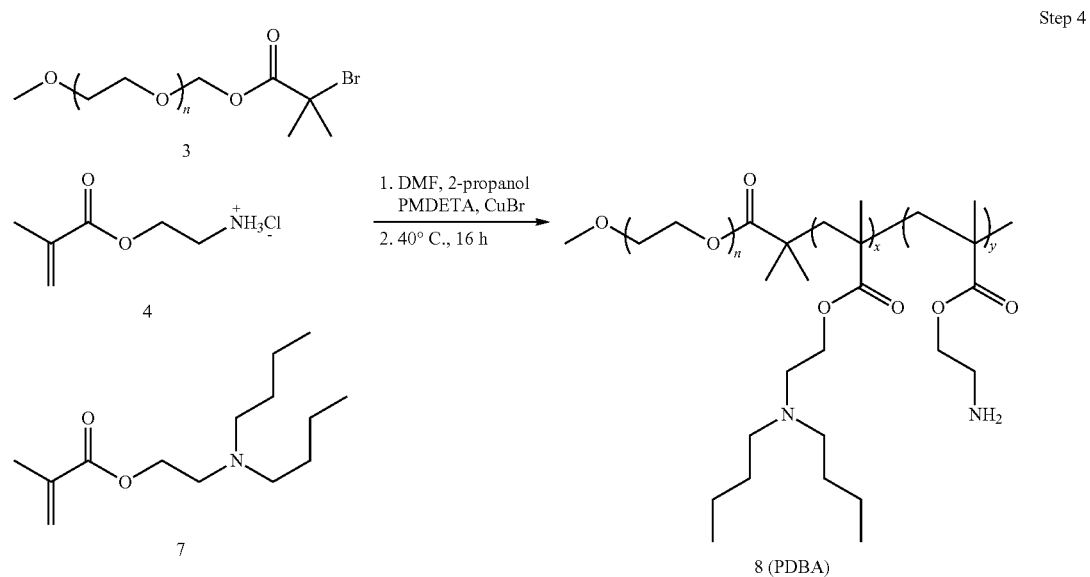
Step 5
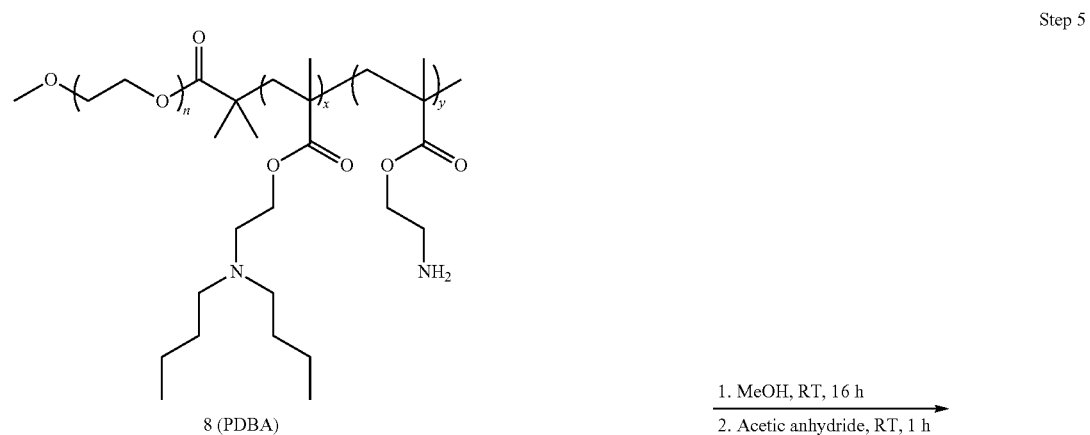
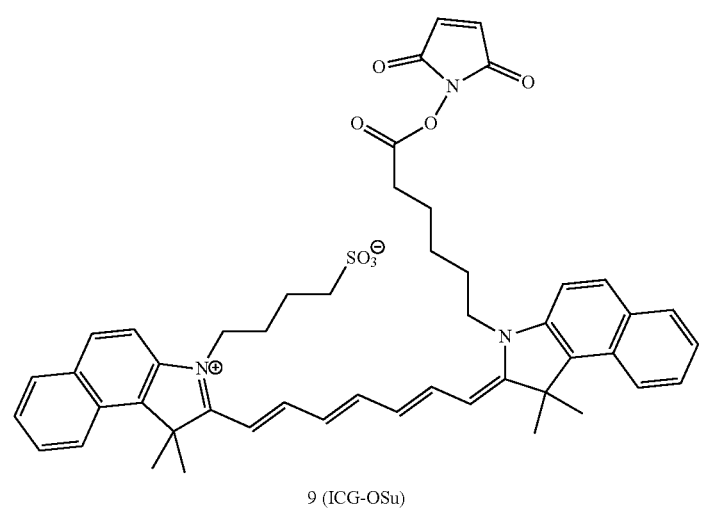

-continued

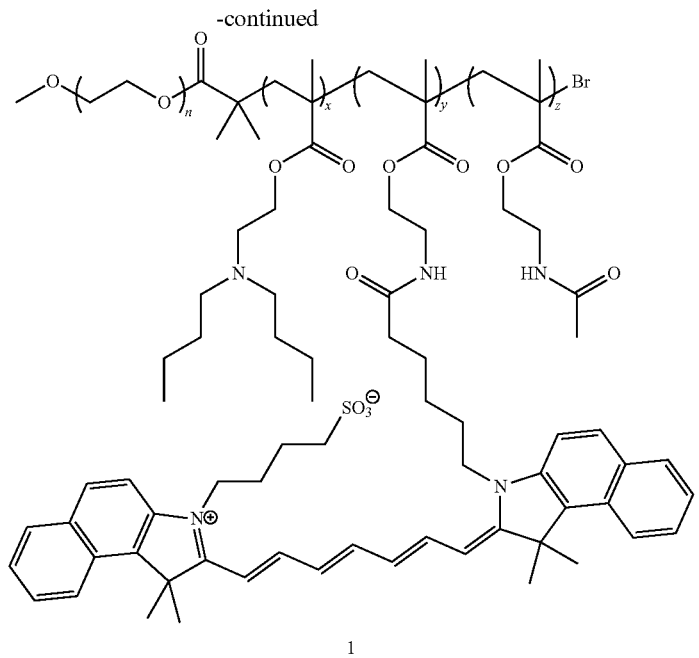

1

Step 4:

Synthesis:

Intermediate 3 was added to a flask and dissolved in a mixture of the dimethylformamide (DMF) and 2-propanol by gently heating the flask. The contents of the flask were allowed to cool to room temperature and 4 and 7 (AMA-MA monomer and DBA-MA monomer, respectively) were added to the solution followed by N,N,N',N'',N''-Pentamethyldiethylenetriamine (PMDETA). The reaction mixture was stirred and then subjected to four freeze-pump-thaw cycles under nitrogen to remove air (oxygen). The reaction mixture was treated with copper (I) bromide (CuBr) while still frozen and was subjected to three cycles of vacuum and flushing with nitrogen to ensure that entrapped air was removed and the reaction was then allowed to warm to 40° C. in an oil bath. The reaction mixture was allowed to further react for 16 hr. At the completion of the reaction, the mixture was diluted with tetrahydrofuran and filtered through a bed of the aluminum oxide ($Al_2O_3$). The solvents were removed from the filtrate using rotary evaporation and dried under vacuum.

Purification:

The dried crude product was dissolved with methanol and purified by tangential flow filtration through a 10 k MWCO Pellicon® 2 Mini Filter cassette with methanol. The solvent was then removed using rotary evaporation. The purified intermediate 8 ($PEO_{113}$-b-($DBAs_{80-150}$-r-$AMA_{1-3}$), PDBA) was dried under vacuum and stored at −80° C. for use in Step 5. A typical yield is 60%-90% with a purity of >93% (HPLC area %). In some cases, the product is a mixture of conjugated and unconjugated polymer.

Step 5:

Synthesis:

Intermediate 8 (PDBA) was dissolved in methanol (MeOH) with the help of a sonication bath. The methanol solution was then added to 9 (ICG-OSu). The reaction was stirred at room temperature for 16 h while protected from light. At the end of the reaction, a 6-fold excess acetic anhydride was added to the reaction mixture and allowed to mix for 1-1.5 h to produce the crude product Compound 1.

Purification:

The crude product purified by tangential flow filtration through a 10 k Pellicon® 2 Mini Ultrafiltration Module with methanol. The solvent of the filtered solution was removed in vacuo to produce Compound 1 which was protected from light and stored at −80° C. A typical yield is >70% with a purity of NLT 95% (SEC).

Analysis:

Analysis of relative molar mass distribution is conducted via a custom gel permeation chromatography (GPC) method with refractive index (RI) detection and two Agilent PLgel Mixed-D 300×7.5 mm columns. Sample chromatograms are compared to a calibration curve constructed from polystyrene standards from 580 to 1,074,000 g/mol to calculate molar mass distribution.

Example 1. Synthesis and Characterization of AZD-UPS NP

Figure 2:
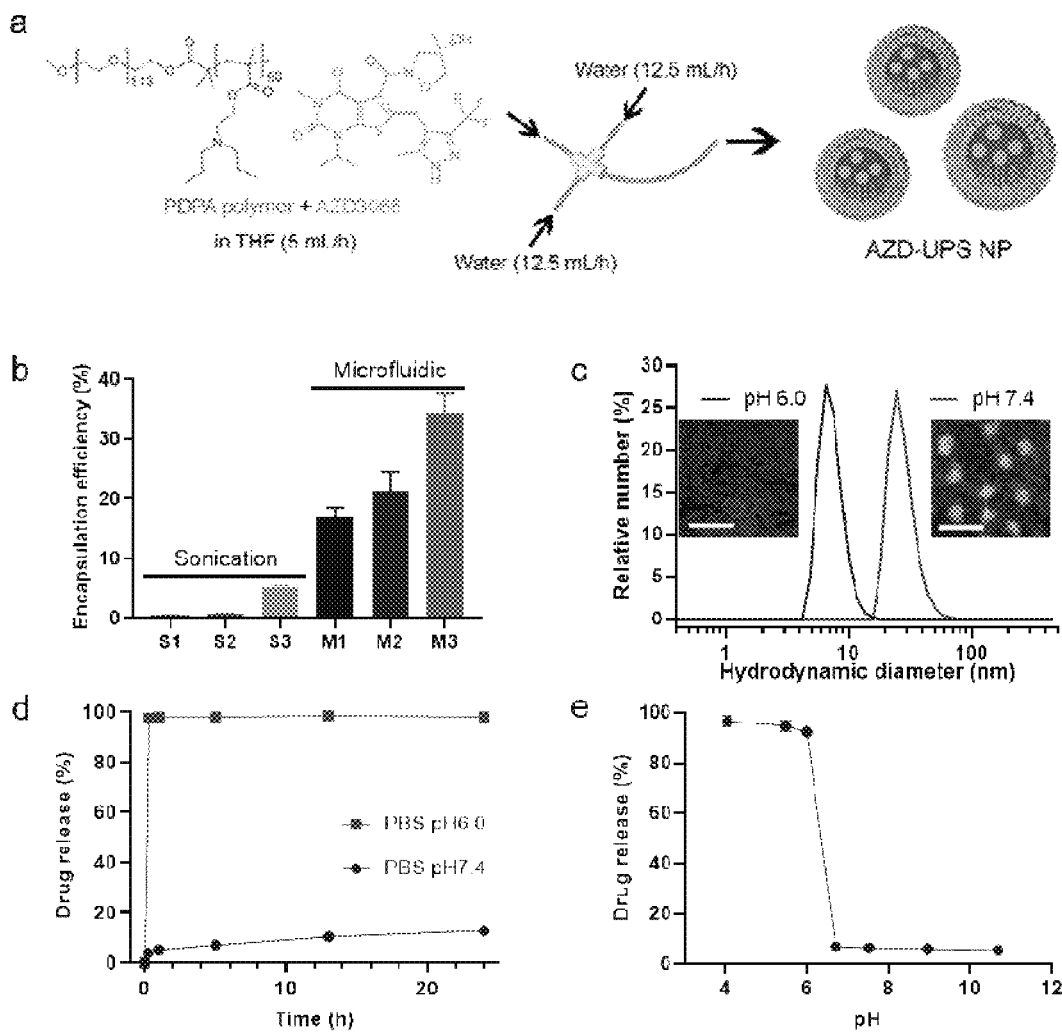
FIG. 2 shows the preparation and characterization of AZD-UPS NPs. (a) Schematic of microfluidic method to produce AZD-UPS NPs. (b) Microfluidic method increases encapsulation efficiency of AZD3965 in UPS nanoparticles over sonication method with different UPS/AZD3965 ratios. (c) Dynamic light scattering and transmission electron microscopy (TEM) analysis of AZD-UPS NPs at pH 7.4 and its dissociation into unimers at pH 6.0. The apparent pKa of the UPS polymer is 6.1. Scale bars=50 nm in the TEM images. (d) pH-dependent drug release from AZD-UPS NPs in phosphate buffered saline (PBS) over 24 h at 37° C. At pH 6.0, instantaneous release of AZD3965 drug was observed after micelle dissociation whereas majority of the drug was kept in the micelles at pH 7.4. (e) A binary drug release profile across the micelle transition pH of the PDPA copolymer was observed from AZD-UPS NPs after 15 min incubation in PBS solution.

The PEG-b-PDPA copolymer was synthesized following the reported procedure using the atom transfer radical polymerization method (ATRP). To formulate drug-loaded micelles, the polymer was first dissolved in tetrahydrofuran (THF) and AZD3965 (Selleck, USA) was dissolved in dimethyl sulfoxide (DMSO). UPS polymer and AZD3965 solutions were mixed together with different mass ratio (5:1 or 10:1). For sonication method, 0.5 mL mixture was added into 4 mL distilled water dropwise under sonication. For microfluidic method, the microfluidic device was set up according to the IDEX method with one central flow, two side flows and one outlet with a curved channel structure (FIG. 2a). The diameter of the flow channel is 152 m. AZD3965 and PDPA polymer in different ratio were dissolved in tetrahydrofuran with 9.1% dimethyl sulfoxide, and introduced to the microfluidic device through the central channel at a flow rate of 5 mL/h. Water was introduced through the two side channels at 12.5 mL/h. Upon mixing in the junction, AZD3965-loaded UPS nanoparticles (AZD-UPS NPs) were generated in a single nanoprecipitation step. The THF was removed by ultrafiltration with (100 kD) membrane for several times. Then distilled water or saline was added to adjust the UPS polymer concentration to 5 mg/mL as a stock solution.

HPLC analyses of AZD3965 were performed using the Agilent 1260 Infinity II System on a Poroshell 120 EC-C18 column, purchased from Agilent Technologies (Palo Alto, Calif., USA). The eluent consists of (A) 0.1% TFA in water and (B) 0.1% TFA in acetonitrile. The peak area at 14.5 min was measured and AZD3965 concentration in solution was obtained from the standard curve. The AZD3965 encapsulation efficiency (EE) and loading density (LD) were then calculated according to the following equations:

$$F.F.\% = \frac{\text{Weight of } AZD3965 \text{ in } NPs}{\text{Weight of } AZD3965 \text{ fed initially}} \times 100\%$$

$$LD\% = \frac{\text{Weight of } AZD3965 \text{ in } NPs}{\text{Weight of } NPs} \times 100\%.$$

After micelle formation, the nanoparticles were characterized by transmission electron microscopy (TEM, JEOL 1200 EX model) for micelle size and morphology, and dynamic light scattering (DLS, Malvern MicroV model, He—Ne laser, $\lambda=632$ nm) for hydrodynamic diameter.

was collected by ultracentrifugation and analyzed by HPLC. Percentage of drug release was quantified as a function of medium pH.

Results:

AZD-UPS NPs exhibit ultra-pH sensitivity across the transition pH of 6.1 for the PDPA polymer (FIG. 6a) comparable to the drug-free PDPA micelles. The particle size and morphology was analyzed by dynamic light scattering (DLS) and transmission electron microscopy (TEM) (FIG. 2c). At pH 7.4, spherical micelles were formed with hydrodynamic diameter of 33.3±0.2 nm; at pH 6.0, which is below the apparent pKa of PDPA (6.1), micelles dissociated into unimers (9.9±2.6 nm in diameter). The pH-dependent release kinetics of the AZD-UPS micelles was quantified by HPLC after micelle incubation with phosphate buffered saline (PBS) solution at pH 7.4 and 6.0 over 24 h (FIG. 2d, FIG. 7a). At pH 7.4, less than 10% of drugs leaked out of the PDPA micelles over 24 h. In contrast, majority (>95%) of the drug was instantaneously released from the micelles at pH 6.0 within 15 mins. Further pH-dependent drug release studies show a binary off/on drug release phenotype after 15 min incubation across the apparent pKa (6.1) of the PDPA polymer (FIG. 2e, FIG. 7b). At pH higher than 6.1, drugs were stably encapsulated inside the PDPA micelles; when pH dropped below 6.1, micelle disassembly led to rapid release and dose dumping

TABLE 1

Comparison of AZD3965-loaded UPS nanoparticles by sonication versus microfluidic method.

| Method | NO. | Initial Weight Ratio PDPA | Initial Weight Ratio AZD | pH | Encapsulation efficiency (Mean ± SD, %) | Loading density (Mean ± SD, %) | Diameter (nm ± SD) | Polydispersity |
|---|---|---|---|---|---|---|---|---|
| Sonication method | S1 | 5 | 1 | 7.4 | 0.45 ± 0.09 | 0.04 ± 0.009 | 86.7 ± 1.7 | 0.34 |
|  | S2 | 10 | 1 | 7.4 | 0.71 ± 0.04 | 0.14 ± 0.008 | 84.5 ± 0.5 | 0.28 |
|  | S3 | 10 | 1 | 9 | 5.1 ± 0.4 | 0.46 ± 0.03 | 82.8 ± 1.9 | 0.22 |
| Microfluidic method | M1 | 5 | 1 | 7.4 | 16.9 ± 1.6 | 2.8 ± 0.3 | 41.4 ± 0.8 | 0.21 |
|  | M2 | 10 | 1 | 7.4 | 21.2 ± 3.4 | 1.7 ± 0.2 | 39.6 ± 0.2 | 0.24 |
|  | M3 | 10 | 1 | 9 | 34.2 ± 3.3 | 3.0 ± 0.3 | 33.3 ± 0.2 | 0.15 |

Table 1 shows a comparison of the three AZD-UPS NPs in antitumor efficacy and synergy with anti-PD-1 therapy. Similar antitumor responses were observed. In the B16F10 tumor model, tumor growth inhibition and survival data in C57BL/6 mice (n=9-10 per group) were analyzed.

Example 2. pH-Dependent Drug Release Studies

Freshly made AZD-UPS NPs were mixed with phosphate buffered saline (PBS) with different pH values (7.4 or 6.0) at 37° C. At different time points, 0.5 mL AZD-UPS NP solution was removed and filtered by ultracentrifugation using 100 kD molecular weight cutoff membranes to collect the free drug. Drug concentration in the filtrate was measured by HPLC and further quantified to the percentage of total amount of loaded drugs.

To evaluate drug release profiles at multiple pH values, freshly made AZD-UPS NPs were first mixed with PBS solution at pH 11. Small volumes (1 μL in increments) of 0.1 M HCl was added to adjust the pH. The pH values were measured using a Mettler Toledo pH meter with a microelectrode. At different pH, 0.5 mL AZD-UPS NP solution was removed after 15 min of incubation and free AZD3965

Example 3. pH Titration Studies

AZD-UPS NPs and drug-free UPS NPs were first diluted to 2.0 mg/mL with deionized water. Sodium chloride was added to adjust the salt concentration to 150 mM. pH of solution was adjusted to 10 using 0.1 M NaOH. pH titration was performed by adding small volumes (1 μL in increments) of 1.0 M HCl solution under stirring. The pH decrease was monitored as a function of the total added volume of HCl.

Example 4. Animals and Cells

All animal procedures were performed with ethical compliance and approval by the Institutional Animal Care and Use Committee at the University of Texas Southwestern Medical Center. Cells were cultured in DMEM medium (10% fetal bovine serum, 100 U/mL penicillin G sodium and 100 μg/mL streptomycin (Pen/Strep), non-essential amino acids, and 20 μM β-mercaptoethanol (β-ME)) at 37° C. in 5% $CO_2$ and the normal level of $O_2$.

Example 5. Measurement of Lactate and pH in the Cell Culture Medium

For lactate measurement, TC-1 cells were cultured in normal DMEM medium as described above with different drugs: free AZD3965 (1 uM), intact AZD-UPS NPs (1 uM effective AZD3965 concentration), or pretreatment of AZD-UPS NPs in pH 6.0 buffer for pH-activated drug release followed by addition into the cell culture medium. After 24 h incubation, lactate concentration was measured by NOVA BioProfile 4. For pH measurement, TC-1 cells were cultured in DMEM medium (D5030, Sigma) without NaHCO$_3$, and in incubator without CO$_2$ for 24 h, followed by measurement of medium pH.

To investigate the drug activity, changes of lactate and pH in the culture medium of TC-1 cancer cells were quantified. Free AZD3965 (1 μM) significantly decreased the secretion of lactate and inhibited the lowering of pH in the medium compared to the untreated control over 24 h (p<0.001, FIG. 3a-b). Intact AZD-UPS NPs (1 μM effective AZD3965 concentration) had no significant effect (p=0.068) on medium pH or lactate concentration primarily due to drug encapsulation in the micelles. Pretreatment of AZD-UPS NPs in pH 6.0 buffer to induce pH-activated drug release followed by addition into the cell culture medium exhibited effects similar to free AZD3965.

Example 6. Seahorse Assay

Extracellular acidification rate (ECAR) of TC-1 cells was measured under different treatment for 2 h by Seahorse XF96 Extracellular Flux Analyzer. Basal conditions without glucose (Bas), with glucose (Glu), at maximum (Max) with the addition of oligomycin (Oli), and inhibited by 2-dexoxy-glucose (2-DG).

Seahorse assay further supported the micelle-modulated drug effect in response to glucose addition (FIG. 7b). These data illustrate AZD-UPS NPs effectively blocked the drug effect in the micelle state; upon pH-triggered drug release, AZD3965 was able to inhibit the export of lactic acid from cancer cells.

Example 7. Pharmacokinetics and Biodistribution Analysis

Mouse plasma were collected and added into 1 mL of methanol/water mixture (80/20, v/v) at 0.5, 6 and 24 h after treatment by different regimens. Tissues (heart, liver, kidney and tumor) were collected at 24 h. About 100 mg of tissues were removed, and the wet weight was recorded. The tissues were homogenized in 1 mL of methanol/water mixture (80/20, v/v). The plasma and tissue mixture were centrifuged and the supernatant was collected respectively, dried by a SpeedVac, then dissolved in methanol and measured by HPLC. AZD3965 were dissolved in DMSO at a concentration of 1 mg/mL. The concentrations of the samples were controlled at 0.05, 0.1, 0.5, 1, 2, 4, 6, 8, and 10 μg/mL to establish the calibration curve.

Figure 3:
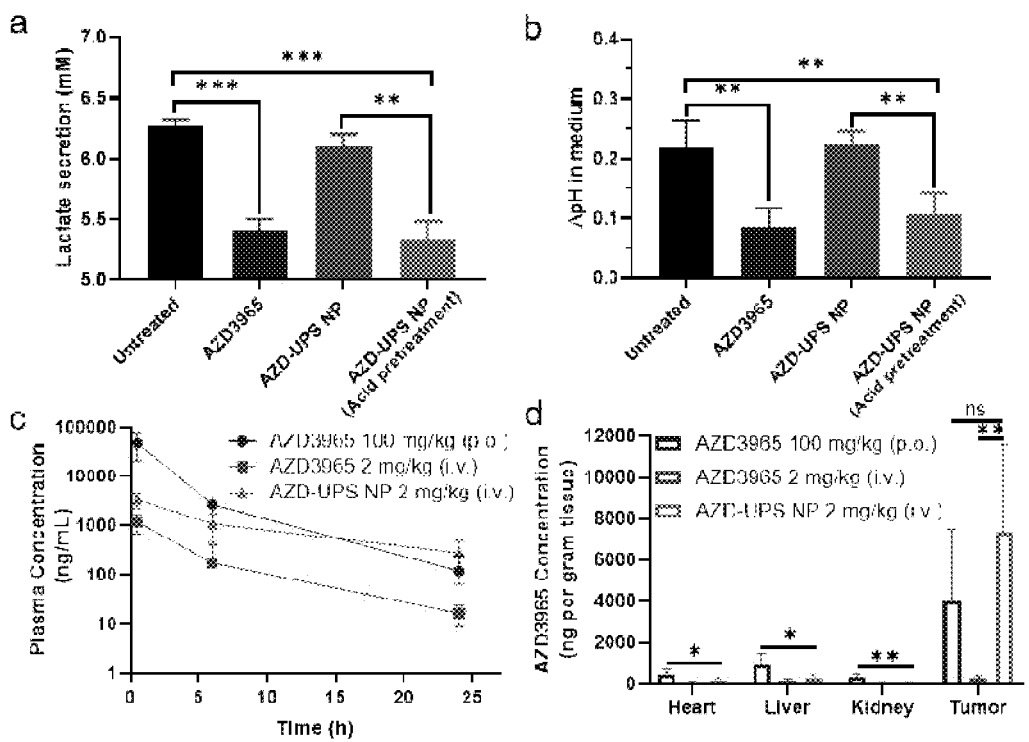
FIG. 3 shows AZD-UPS NPs inhibited export of lactic acid from cancer cells and improved drug pharmacokinetics in a mouse tumor model. AZD3965 alone or pretreatment of AZD-UPS NP at pH 6.0 effectively decreased lactate secretion (a) and pH change (b) in the cell culture medium at 24 h. Intact AZD-UPS NPs at pH 7.4 did not affect the lactate secretion or pH change compared to the control groups. (c) Plasma concentration of AZD3965 following oral administration (100 mg/kg), intravenous administration of AZD3965 alone and AZD-UPS NP at the same drug dose (2 mg/kg). (d) AZD3965 distribution in heart, liver, kidney and tumor tissues 24 h after administration. AZD3965 concentrations were normalized per gram of tissue and expressed as ng/g. *P<0.001, P<0.01, *P<0.05 (nonparametric Student's t-test).
Figure 8:
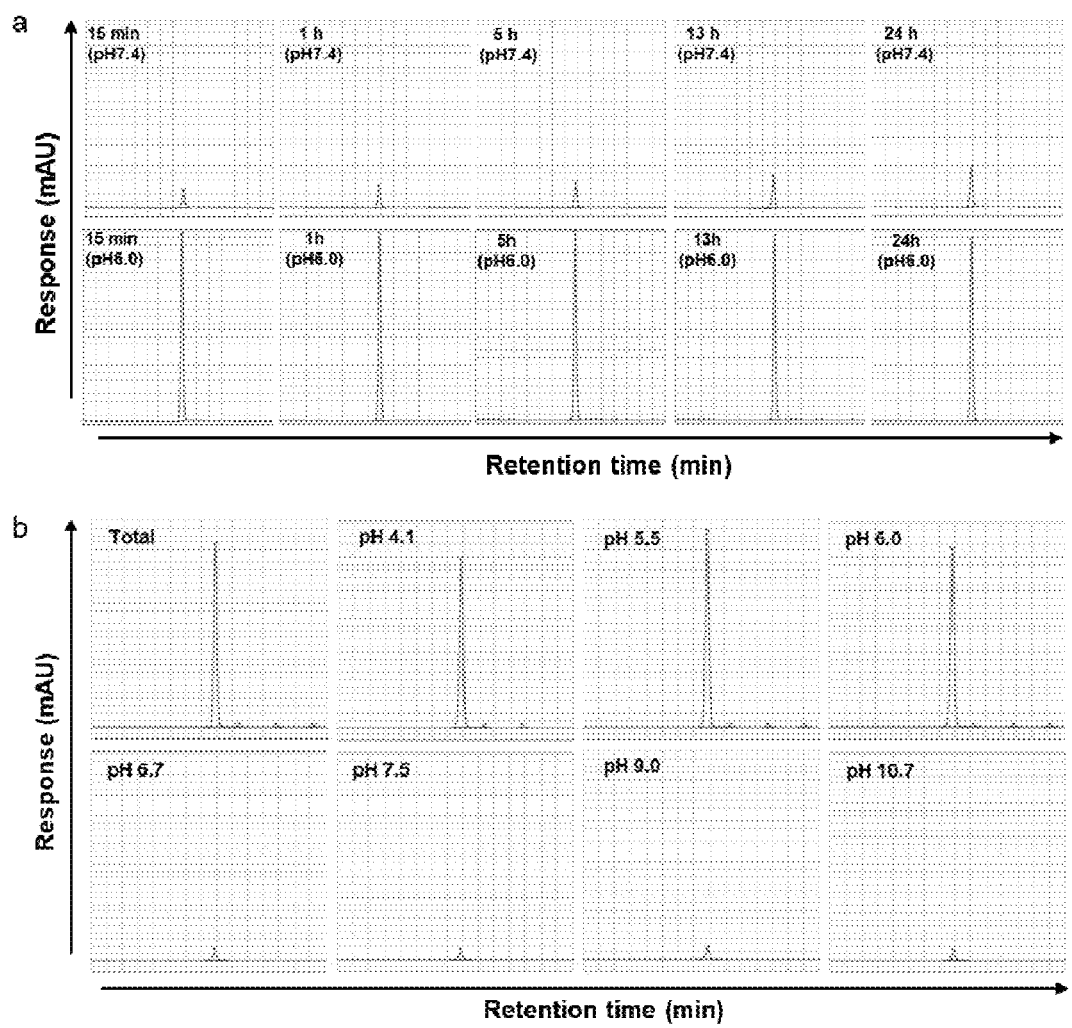
FIG. 8 (a) Representative HPLC chromatograms of pH-dependent drug release from AZD-UPS NPs in phosphate buffered saline (PBS) over 24 h at 37° C. At pH 6.0, instantaneous release of AZD3965 drug was observed after micelle dissociation whereas majority of the drug was kept in the micelles at pH 7.4. (b) Representative HPLC chromatograms of drug release profiles over different medium pH from AZD-UPS NPs. In a-b, retention time intervals are from 10.5 to 18 min in X axis; response is from −0.2 to 50 mAU in Y axis.

TC-1 tumor-bearing mice were used to evaluate the pharmacokinetics and biodistribution of AZD3965 drug from different formulations. AZD3965 by oral administration (100 mg/kg, dose recommended by AstraZeneca) exhibited rapid oral absorption and high peak drug concentration of 47±27 μg/mL at 30 min (FIG. 3c). In contrast, intravenous injection of AZD-UPS NP at much reduced dose (2 mg/kg) resulted in significantly decreased peak concentration (3.3±1.2 μg/mL) at 30 min but comparable plasma concentrations at 24 h. Intravenous injection of free AZD3965 drug at the same dose as AZD-UPS-NP (i.e., 2 mg/kg) showed rapid clearance of the drug. The area under the concentration-time (AUC) value of AZD-UPS NP is 24±7 μg/mL·h, approximately 4.5-fold over free AZD3965 (5.4±2.5 μg/mL·h). Tissue distribution analysis was performed in the heart, liver, kidney and tumor tissues 24 h after the administration (FIG. 3d). AZD-UPS NP achieved significantly higher levels of tumor accumulation of the AZD3965 drug (7.4±4.2 μg/g of tissue) over free drug (0.29±0.12 μg/g, p=0.0049). AZD-UPS NP delivered even higher drug dose to the tumors over oral administration of a 50-fold higher dose of AZD3965 (4.0±3.5 μg/g). In contrast, drug distribution in the heart and liver tissues was significantly reduced in AZD-UPS NP group over oral administration of AZD3965. Safety evaluations show AZD-UPS NP and oral administration of AZD3965 did not cause weight loss during two weeks of treatment (FIGS. 8a-b), while oral administration of AZD3965 significantly increased the levels of cardiac troponin-I (cTnI), alanine aminotransferase (ALT), and aspartate aminotransferase (AST), indicating that encapsulating AZD3965 into UPS NP can reduce liver and cardiac toxicities (FIGS. 8c-d).

Example 8. Tumor Inoculation and Treatment

Six to eight week old mice (n=5-7 for each group) were injected subcutaneously with TC-1 (2×10$^5$) or B16F10 (2×10$^5$) cells into the right flank. Animals were treated by 50 mg/kg AZD3965 (administered twice daily by oral gavage for a total of 7 days), or by AZD-UPS NPs (containing 2 mg/kg AZD3965, IV injected at days 7, 10 and 13). Some groups were intraperitoneally injected with 200 μg checkpoint inhibitors (anti-mPD-1, BioXcell, BE0146) for comparison or synergy evaluation. Tumor growth was subsequently measured twice a week using a digital caliper and calculated as 0.5×length×width×height by blinded investigators. Mouse weight was also recorded. Mice were sacrificed when the tumor volumes reached 1,500 mm$^3$.

Figure 4:
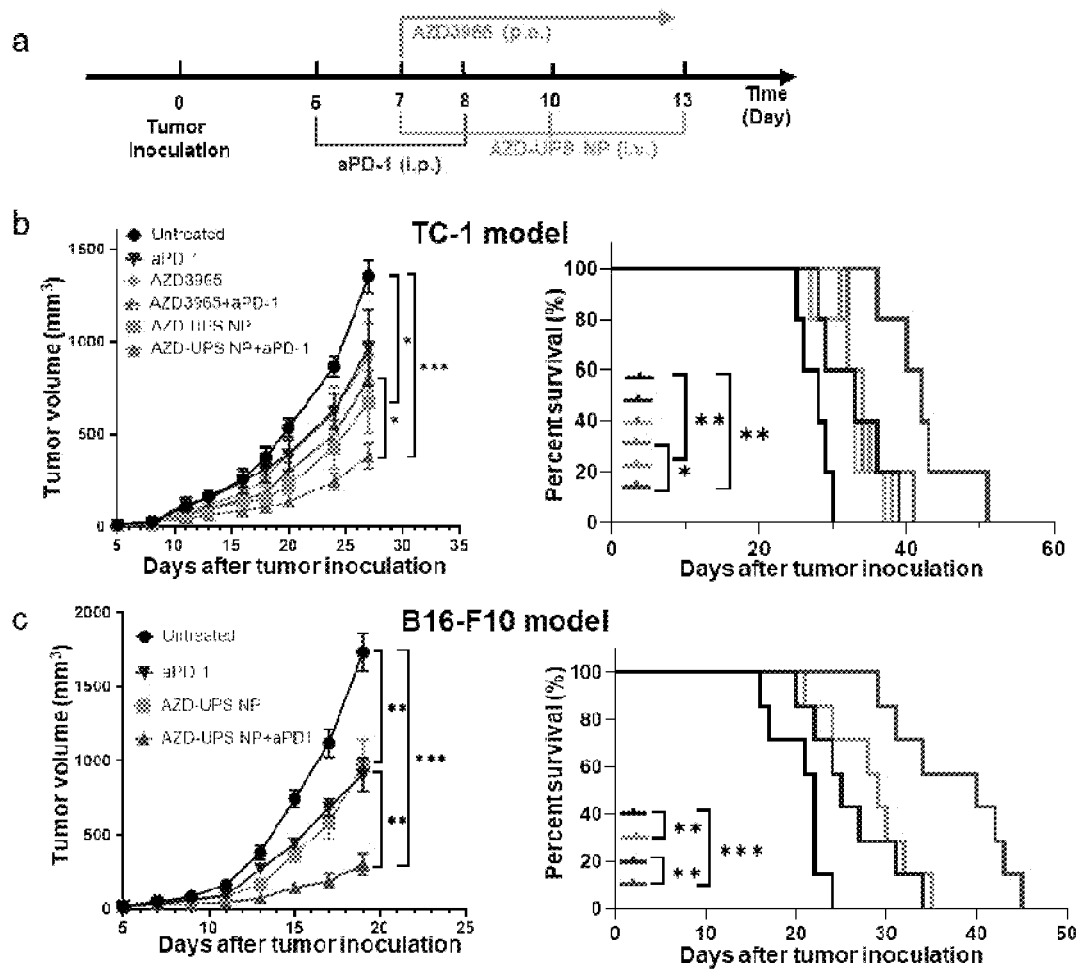
FIG. 4 shows AZD-UPS NP showed antitumor efficacy and synergy with anti-PD-1 therapy. (a) Treatment regimen in TC-1 and B16F10 tumor models. (b) In TC-1 model, C57BL/6 mice (n=5 per group) were inoculated with $2 \times 10^5$ TC-1 tumor cells and treated with different drugs. Tumor growth and Kaplan-Meier survival curves are shown. (c) In the B16F10 tumor model, tumor growth inhibition and survival data in C57BL/6 mice (n=7 per group) were analyzed.

Results:

Results show in the TC-1 model, treatment with AZD-UPS NP led to significant tumor growth inhibition (tumor volume=6.7±3.8×10$^2$ mm$^3$) over untreated group (1.4±0.2× 10$^3$ mm$^3$, p=0.01) on day 27 after tumor inoculation, whereas orally administrated AZD3965 (9.2±4.1×10$^2$ mm$^3$, p=0.09) showed insignificant differences over control (FIG. 4b). The synergistic effect of AZD-UPS NPs with anti-PD-1 treatment was also detected in the TC-1 model (3.8±1.5×10$^2$ mm$^3$), which is significantly better than the combination of oral AZD3965 and anti-PD1 (8.0±3.1×10$^2$ mm$^3$, p=0.025). Long-term survival was also improved (p=0.023) between the two groups. The therapeutic synergy in combining AZD-UPS NP with anti-PD1 therapy was further validated in the B16F10 melanoma tumor model. Reduction in tumor growth (p<0.01) and prolonged survival (p<0.01) were observed in the combination group over any single arm control (FIG. 4c). These results support the premise that inhibiting tumor acidosis can improve response to anti-PD-1 treatment.

Example 9. Toxicity Analysis

Tumor-bearing mice were treated with 50 mg/kg AZD3965 (administered by oral gavage for a total of 7 days) or AZD-UPS NPs (containing 2 mg/kg AZD3965, IV injected at days 7, 10 and 13). Blood of different mouse groups were collected after 4 h. Then alanine transaminase activity assay (Abcam, ab105134), aspartate aminotransferase activity assay (Abcam, ab105135), and mouse cardiac troponin-I ELISA analysis (Life Diagnostics, Inc., Cat. No. CTNI-1-HS) were performed.

Example 10. Flow Cytometry Analysis

Tumor tissues were digested by 1 mg/mL collagenase IV (Sigma-Aldrich) and 0.2 mg/mL DNase I (Sigma-Aldrich) for 45 min at 37° C. Cells were then stained with anti-CD16/CD32 (Biolegend, Cat #: 101301, clone: 93), Viability 405/520 Fixable Dye (Miltenyi), CD45.2 APC-CY7 (Biolegend, Clone: 104), CD3e FITC (Biolegend, Clone: 17A2), CD8a PE-vio615 (Miltenyi, Clone: REA601), Tetramer/PE—He2Db HPV 16 E7 (RAHYNIVTF) (MBL), PD-1 PE (Biolegend, Clone: 29F.1A12), TIM-3 APC (Miltenyi, Clone: REA602), CD4 VioBlue (Miltenyi, Clone: REA604), and Foxp3 PE (Miltenyi, Clone: REA788) antibodies, according to the manufacturer's protocols. Flow data were collected on a BD™ FACS LSRFortessa SORP flow cytometer and analyzed with FlowJo (Tree Star Inc., Ashland, Oreg.).

Example 11. Statistical Analysis

Based on pilot immunization and tumor treatment studies, group sizes of five animals/group were used for immunogenicity measurements and five to seven animals/group for tumor therapy experiments. Statistical analysis was performed using Microsoft Excel and Prism 5.0 (GraphPad). Data are expressed as means±SEM or means±SD. Data were analyzed by Student's t-test. All t-tests were one-tailed and unpaired, and were considered statistically significant if $p<0.05$ (*, $p<0.05$; , $p<0.01$; *, $p<0.001$ unless otherwise indicated). The survival rates of the two groups were analyzed using a log-rank test and were considered statistically significant if $p<0.05$.

Example 12. Combination Studies with Anti-PD1 Therapy

Figure 5:
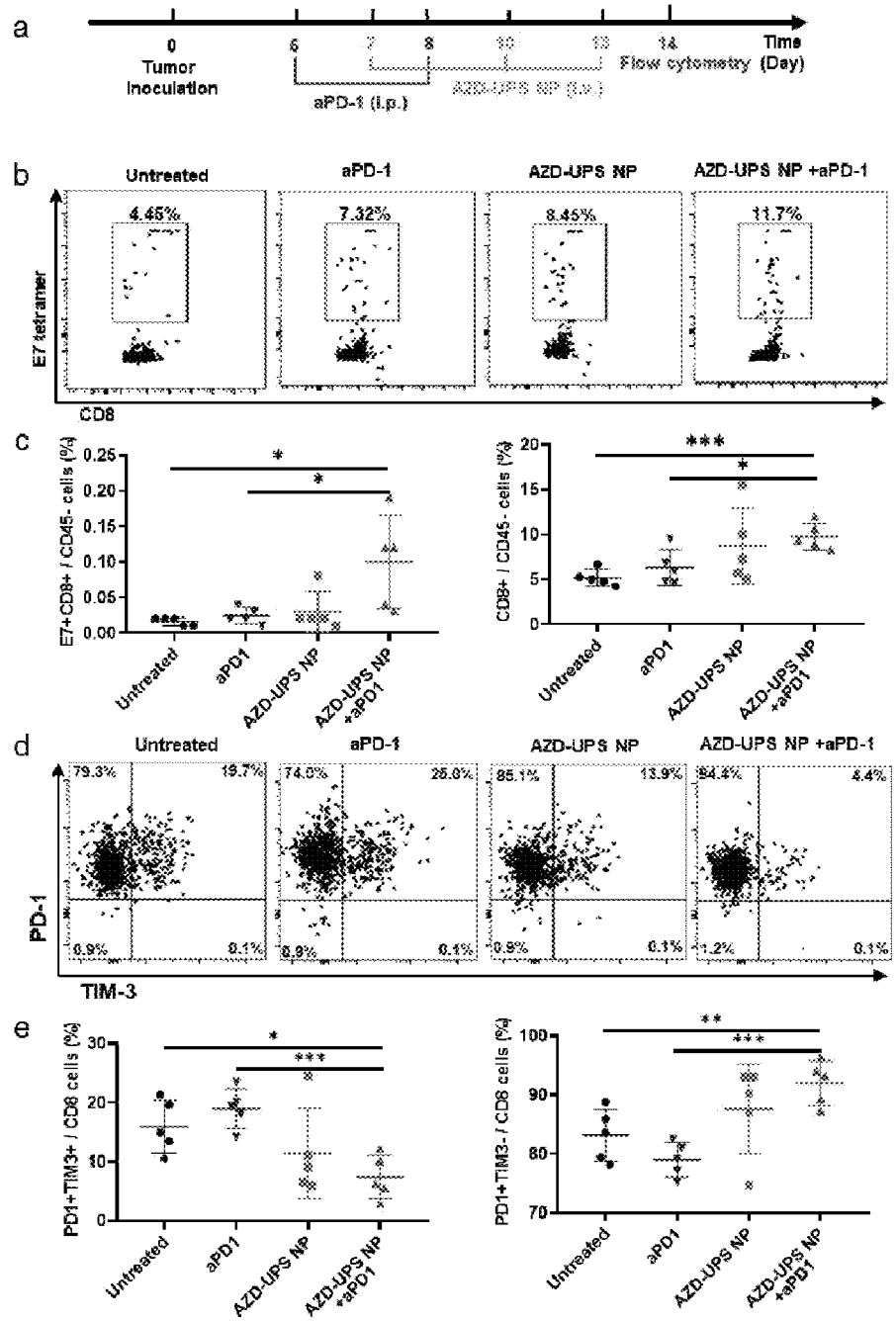
FIG. 5 shows immune profiles of the TC1 tumor after different treatment regimens. (a) Scheme of the flow cytometry analysis of TC-1 tumors. (b) Representative flow dot plots of $H-2D^b$ HPV16 E7 (RAHYNIVTF) tetramer staining of CD8+ T cells in the tumor. (c) Flow cytometry data show the significant increase of E7-specific CD8+ T cells after combined treatment of AZD-UPS NP with anti-PD1. (d) Representative flow dot plots of PD1 and TIM3 of CD8+ T cells in the tumor after treatment. (e) Flow cytometry data show the decrease of $PD1^+$ $Tim3^+$ CD8 T cells and increase of $PD1^+$ $Tim3^-$ CD8 T cells in TC-1 tumors after combined treatment. In c and e, data are presented as means±SD. Statistical significance was calculated by Student's t-test: *P<0.001, P<0.01, *P<0.05.
Figure 6:
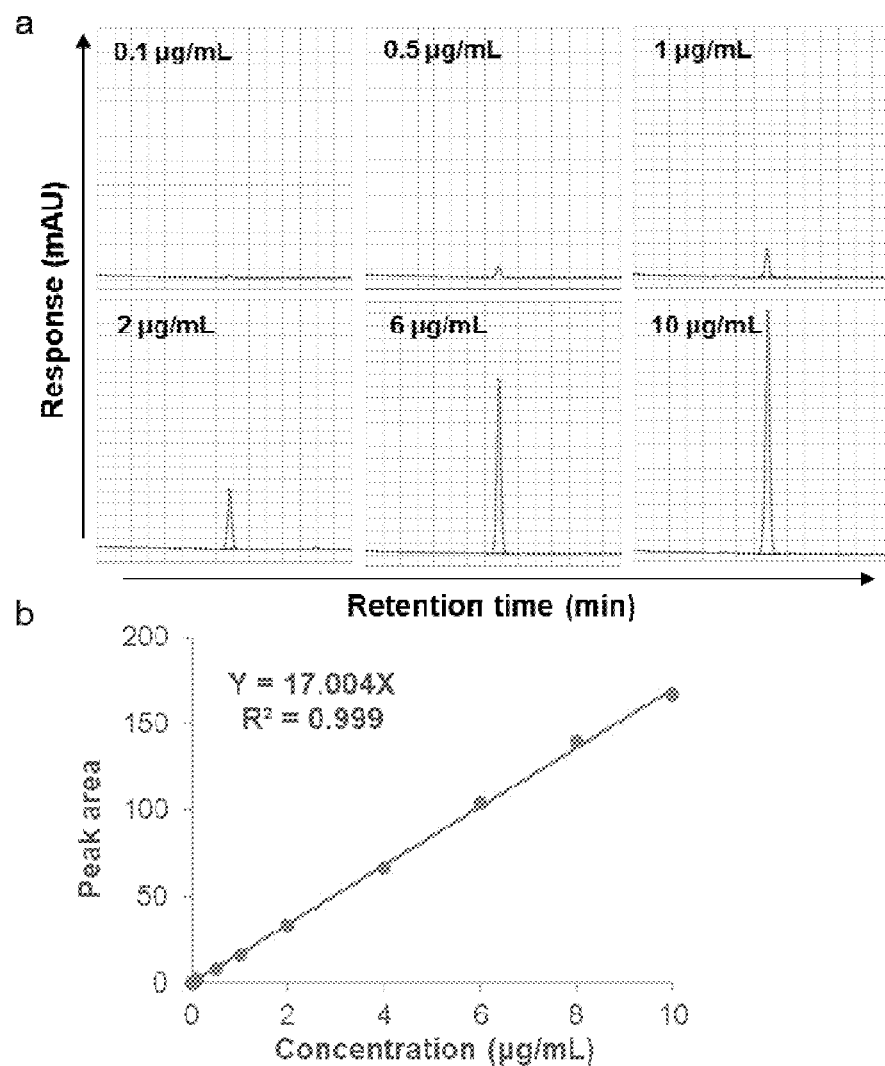
FIG. 6 shows analytical analysis of AZD396. (a) Representative HPLC chromatograms of AZD3965 in water (retention time intervals are from 10.5 to 18 min in X axis; response is −0.2 to 20 mAU in Y axis, and peak elution time of AZD3965 appears at 14.5 min). (b) Standard curve of AZD3965 peak area over drug concentration. Linearity range: 0.05-10 μg/mL.
Figure 7:
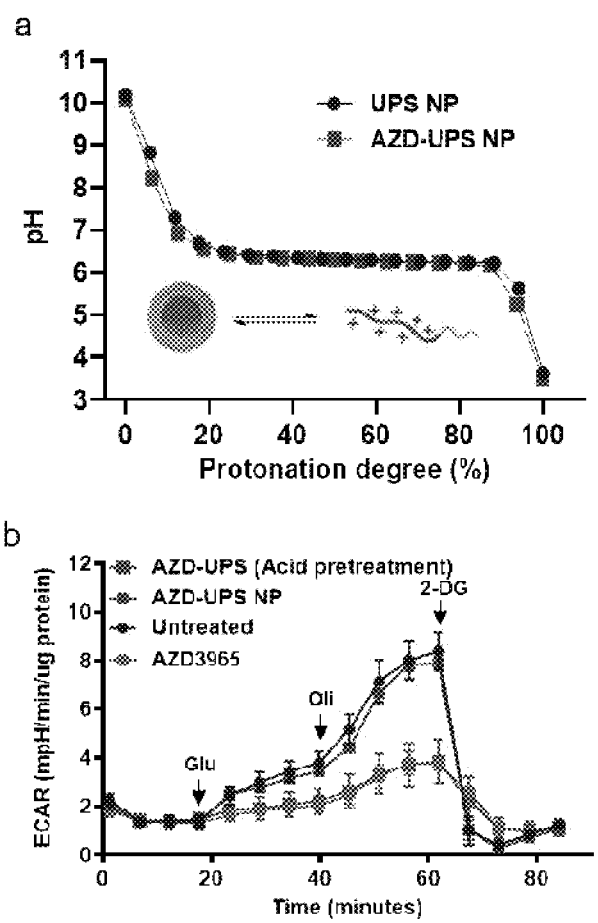
FIG. 7 shows pH titration curves. (a) pH titration curves of drug-free UPS and AZD-UPS nanoparticles show a sharp pH transition in saline solution. Drug loading did not affect the pH response of the polymer carriers. (b) Seahorse analysis of extracellular acidification rate (ECAR) of TC-1 cells with different treatments for 2 h. ECAR data was measured under basal conditions without glucose (Bas), with glucose (Glu), at maximum (Max) with the addition of oligomycin (Oli), and inhibited by 2-DG.
Figure 9:
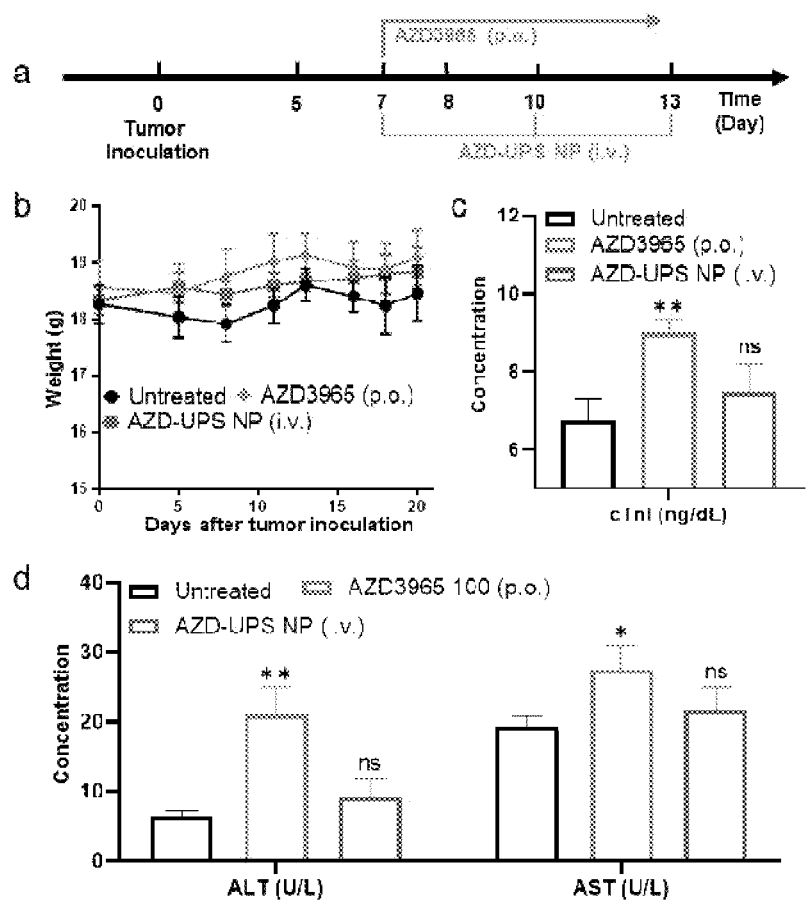
FIG. 9 displays safety evaluation of oral administration of free AZD3956 and intravenous injection of AZD-UPS nanodrug. (a) Scheme of the treatment regimens in the TC-1 tumor model. (b) Body weight curve of different group of mice. Cardiac troponin-I (cTnI, c), ALT and AST levels (d) in serum of different groups at 4 h after last treatment on day 13. Statistical significance is calculated vs. untreated group by Student's t-test: **P<0.01, *P<0.05, ns for not significant.
Figure 10:
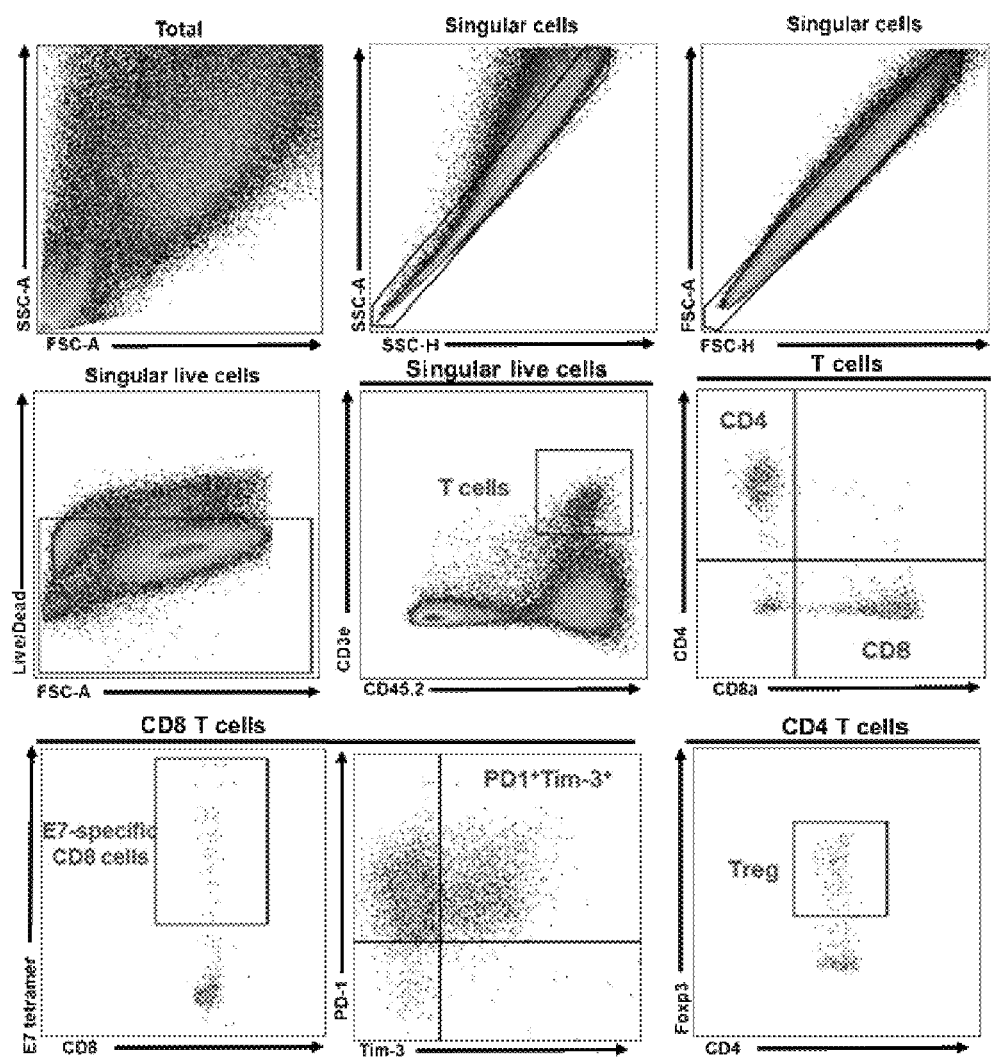
FIG. 10 displays gating strategy for flow cytometry analysis of living singular cells (live/dead-), T cells (CD45+CD3+), CD4+ T cells (CD4+), CD8+ T cells (CD8+), PD-1$^+$Lag-3$^+$ CD8 T cells, PD-1$^+$Tim-3$^+$ CD8 T cells, E7-specific CD8+ T cells, Treg(CD4+Foxp3+) in TC-1 tumor from C57BL/6 mice.
Figure 11:
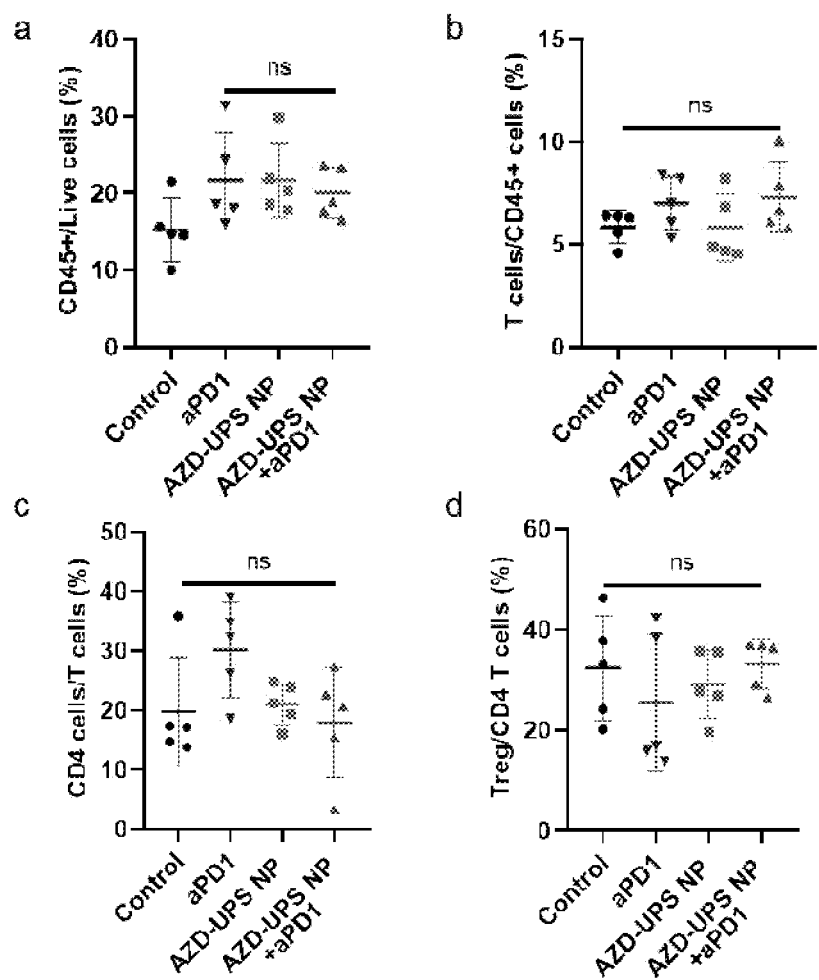
FIG. 11 displays flow cytometry results show total leucocytes (CD45+) (a), T cells (CD45+CD3+) (b), CD4 T cells (c), and Tregs (CD4+Foxp3+) (d) in TC-1 tumors from C57BL/6 mice. Data are presented as means±SEM. Statistical significance was calculated by Student's t-test. These cells were found not significant (ns) from any of the treated groups over untreated control.
Figure 12:
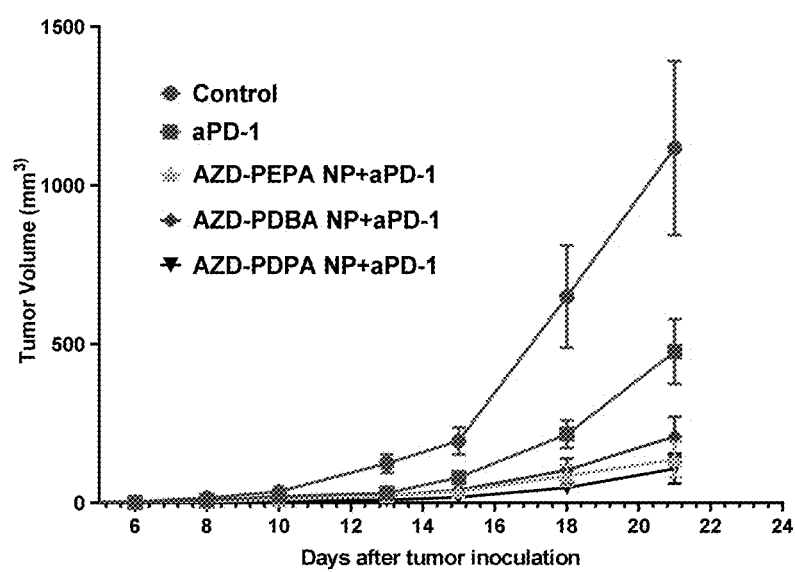
FIG. 12 displays three AZD-UPS nanoparticle compositions in antitumor efficacy and synergy with anti-PD-1 therapy. In the B16F10 tumor model, tumor growth inhibition and survival data in C57BL/6 mice (n=9-10 per group) were analyzed.

Changes in immune profiles after treatment with anti-PD1 alone, AZD-UPS NP alone or combination therapy in the TC1 tumors were investigated (FIG. 6a). The ratio of tumor-infiltrating T-cells over cancer cells (CD45⁻) from different groups was examined. Tumor tissues were dissociated into single cells and the percentage of infiltrating T-cells were analyzed by flow cytometry. Compared to the untreated mice, AZD-UPS NPs alone or anti-PD-1 alone did not significantly increase tumor infiltrating T-cells (CD45⁺ CD3⁺ cells, $p>0.05$) or antigen-specific CD8⁺ T-cells (E7 tetramer⁺ CD8⁺ CD3⁺ cells, $p>0.05$) compared to untreated group (FIG. 5b-c, FIG. 9). In contrast, AZD-UPS NPs with anti-PD-1 treatment results in significant increase of both tumor infiltrating T cells ($p=0.022$) and antigen-specific CD8⁺ T-cells ($p=0.0004$), which supports the correlation of anti-tumor efficacy with T-cell infiltration inside the tumors. Previous studies reported that PD1⁺Tim3⁻ CD8+ T cells have better cytotoxic functions whereas co-expression of PD1 and TIM3 is associated with T-cell exhaustion. AZD-UPS NPs with anti-PD-1 treatment showed distinctively increased PD1⁺Tim3⁻ effector and decreased PD1⁺Tim3⁺ CD8 T cell responses, compared to single arm controls (FIG. 4d-e). The number of CD4+ T cells and Tregs between different treatment groups exhibited no significant changes (FIG. 11). These results illustrate anti-PD-1 alone or AZD-UPS NP alone were not able to prime a durable immune response to TC-1 tumors due to the immunosuppressive effects of tumor acidosis, while the combination led to a significant improvement in CD8 T cell responses against tumors.

In combination with checkpoint blockade, AZD-UPS nanodrug effectively inhibited tumor growth by enhancing antigen-specific CD8 T cell immunity against tumors. This study establishes the preclinical proof of concept to target monocarboxylate transporters to prime tumor microenvironment to augment cancer immunotherapy and to exploit the biological activity of a protein target to improve drug delivery specificity and efficacy.

What is claimed is:
1. A micelle, comprising:
(i) a block copolymer, or a pharmaceutically acceptable salt, solvate, or hydrate thereof, the block copolymer comprising:

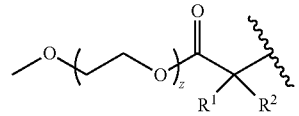

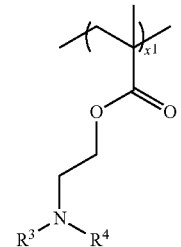

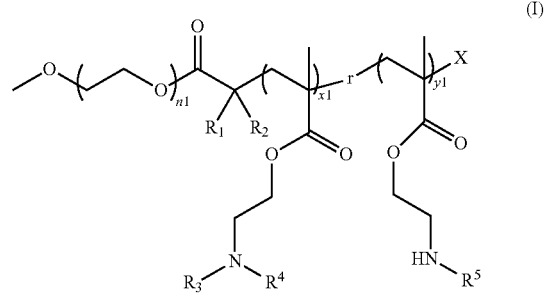

wherein:
$R^1$ and $R^2$ are each independently hydrogen or an optionally substituted $C_1$-$C_6$ alkyl;
$R^3$ and $R^4$ are each independently an optionally substituted $C_1$-$C_6$ alkyl, $C_3$-$C_{10}$ cycloalkyl or aryl;
or $R^3$ and $R^4$ are taken together with the corresponding nitrogen to which they are attached form an optionally substituted 5 to 7-membered ring;
$n_1$ is an integer from 10-200;
$x_1$ is an integer from 20-300;
$y_1$ is an integer from 0-10;
X is a halogen, —OH, or —C(O)OH; and
$R^5$ is hydrogen or a fluorescent dye; and (ii) a therapeutic agent encapsulated by the block copolymer, wherein the therapeutic agent is a monocarboxylate transport inhibitor having the formula:

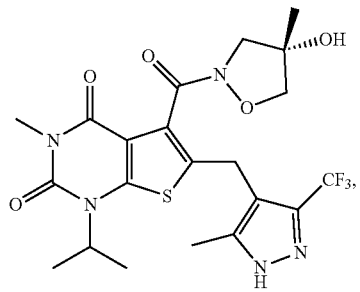

(AZD3965)

or a pharmaceutically acceptable salt, solvate, or hydrate thereof.

2. The micelle of claim 1, wherein, $R^1$ and $R^2$ are each independently —$CH_3$.

3. The micelle of claim 1, wherein the block copolymer is of Formula (II), or a pharmaceutically acceptable salt, solvate, hydrate, or isotopic variant thereof:

Formula (II)

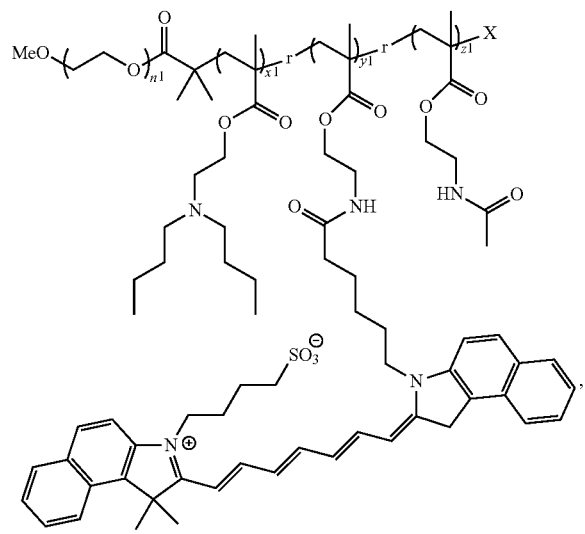

wherein:
X is a halogen, —OH, or —(O)OH;
n is 90-140;
$x_1$ is 50-200;
$y_1$ is 0-3; and
$z_1$ is 0-3.

4. The micelle of claim 1, wherein the block copolymer of Formula (I) has the structure of Formula (Ic), or a pharmaceutically acceptable salt, solvate, or hydrate thereof:

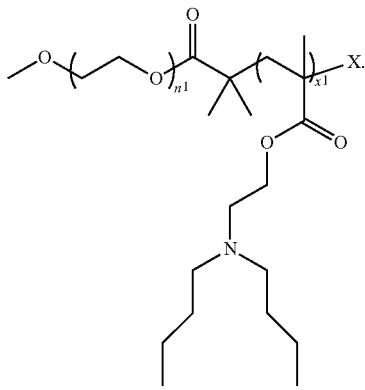

(Ic)

5. The micelle of claim 1, wherein the monocarboxylate transport (MCT) inhibitor is:

(AZD3965)

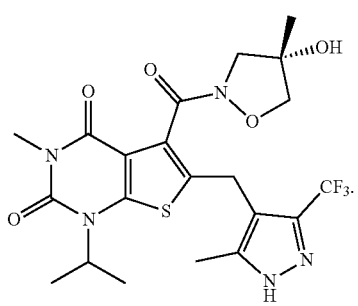

6. A method for treating cancer, wherein the cancer is skin cancer or lung cancer, in a patient in need thereof, comprising administering to the patient a therapeutically effective amount of a micelle of claim 1.

7. The method of claim 6, wherein the cancer is a solid tumor.

8. The method of claim 6, wherein the tumor is reduced in size by about 50%, about 60%, about 70%, about 80%, about 90%, or about 95%.

9. The method of claim 6, wherein the micelle is administered with an additional therapy.

10. The method of claim 9, wherein the additional therapy is a checkpoint inhibitor.

11. The method of claim 10, wherein the checkpoint inhibitor is an anti-PD-1 therapy, anati-PD-L1 therapy, or anti-CTLA-4 therapy.

12. The micelle of claim 1, wherein the block copolymer of Formula (I) has the structure of Formula (Id), or a pharmaceutically acceptable salt, solvate, or hydrate thereof:

(Id)

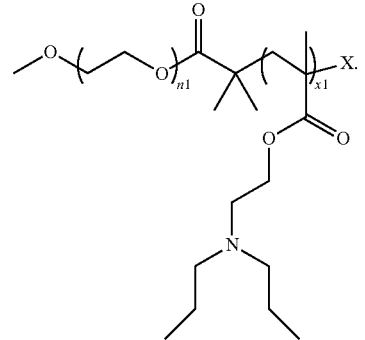

13. The micelle of claim 1, wherein the block copolymer is of Formula (III), or a pharmaceutically acceptable salt, solvate, hydrate, or isotopic variant thereof:
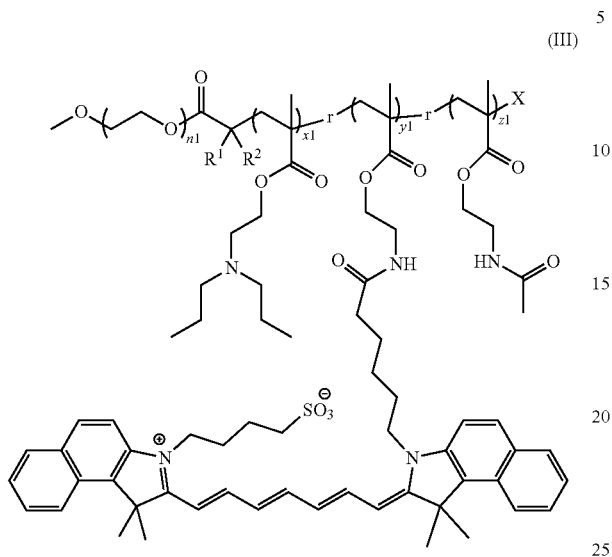
(III)
wherein:
  $X^1$ is a halogen, —OH, or —(O)OH;
  n is 90-140;
  $x_1$ is 50-200;
  $y_1$ is 0-3; and
  $z_1$ is 0-3.
* * * * *